(12) United States Patent
Arini et al.

(10) Patent No.: US 7,369,696 B2
(45) Date of Patent: *May 6, 2008

(54) CLASSIFICATION OF CELLS INTO SUBPOPULATIONS USING CELL CLASSIFYING DATA

(75) Inventors: Nick Arini, Cardiff (GB); Alla Zaltsman, Cardiff (GB); Ian Goodyer, Eastbourne (GB); Yuriy Alexandrov, St. Catharines (CA); Jurek Cybuch, St. Catharines (CA); Bohdan Soltys, St. Catharines (CA); Louis Dagenais, St. Catharines (CA); Liz Roquemore, Cardiff (GB); Sam Murphy, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 547 days.

This patent is subject to a terminal disclaimer.

(21) Appl. No.: 10/817,213

(22) Filed: Apr. 2, 2004
(Under 37 CFR 1.47)

(65) Prior Publication Data

US 2005/0207633 A1  Sep. 22, 2005

(30) Foreign Application Priority Data

Apr. 2, 2003 (GB) ................................. 0307684.1
Nov. 28, 2003 (GB) ................................. 0327651.6

(51) Int. Cl.
*G06F 19/00* (2006.01)
*G06F 7/08* (2006.01)
*G06K 9/00* (2006.01)

(52) U.S. Cl. .............. 382/133; 382/224; 382/128; 382/228; 382/129; 702/21; 435/6

(58) Field of Classification Search ............... None
See application file for complete search history.

(56) References Cited

U.S. PATENT DOCUMENTS

| | | | | |
|---|---|---|---|---|
| 5,757,954 A * | 5/1998 | Kuan et al. | ................. | 382/133 |
| 5,933,519 A * | 8/1999 | Lee et al. | ................. | 382/133 |
| 6,137,899 A * | 10/2000 | Lee et al. | .................. | 382/133 |
| 6,453,060 B1 * | 9/2002 | Riley et al. | ................. | 382/133 |
| 6,804,385 B2 * | 10/2004 | Eisfeld et al. | ............. | 382/128 |
| 7,117,098 B1 * | 10/2006 | Dunlay et al. | ................ | 702/21 |
| 2004/0071328 A1 * | 4/2004 | Vaisberg et al. | ............ | 382/129 |
| 2006/0127881 A1 * | 6/2006 | Wong et al. | ................... | 435/4 |
| 2006/0247862 A1 * | 11/2006 | Arini et al. | ................... | 702/19 |

* cited by examiner

*Primary Examiner*—Bhavesh M. Mehta
*Assistant Examiner*—Mia M Thomas
(74) *Attorney, Agent, or Firm*—Dwayne L. Bentley

(57) ABSTRACT

A method of classifying cells into subpopulations using cell classifying data is described. The method comprises receiving and analyzing image data to identify object areas in the image data to determine, for at least one selected first cell, one or more measurements. A first parameter set is derived from the measurements for the first cell, the first parameter set comprising at least one of said one or more measurements. The first set of cells are classified into subpopulations, and identified to produce first identifying data. Cell classifying data for use in classifying a second set of cells into subpopulations is derived from the first parameter set and the first identifying data. A second set of cells is classified into subpopulations on the basis of one or more measurements taken for cells in the second set of cells, by use of the cell classifying data. The parameter sets of cells may be represented as vectors in an n-dimensional space.

31 Claims, 12 Drawing Sheets

G0/G1/S     G2     Prophase     Mitosis

Metaphase     Anaphase     Telophase     Cytokinesis

SEQUENCE LISTING

<160> NUMBER OF SEQ ID NOS: 2

<210> SEQ ID NO 1
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 1
gggaagctta ggatggcgct ccgagtcacc aggaac                              36

<210> SEQ ID NO 2
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 2
gccggatccc acatattcac tacaaaggtt                                     30

CLASSIFICATION OF CELLS INTO SUBPOPULATIONS USING CELL CLASSIFYING DATA

FIELD OF THE INVENTION

The invention relates to methods of cell classification. Cells are imaged and classified into subpopulations. The invention further relates to apparatus and computer software adapted to carry out such a method.

BACKGROUND OF THE INVENTION

There is currently a need in drug discovery and development and in general biological research for methods and apparatus for accurately performing cell-based assays. Cell-based assays are advantageously employed for assessing the biological activity of chemical compounds.

In addition, there is a need to quickly and inexpensively screen large numbers of chemical compounds. This need has arisen in the pharmaceutical industry where it is common to test chemical compounds for activity against a variety of biochemical targets, for example, receptors, enzymes and nucleic acids. These chemical compounds are collected in large libraries, sometimes exceeding one million distinct compounds. The use of the term chemical compound is intended to be interpreted broadly so as to include, but not be limited to, simple organic and inorganic molecules, proteins, peptides, nucleic acids and oligonucleotides, carbohydrates, lipids, or any chemical structure of biological interest.

In the field of compound screening, cell-based assays are run on populations of cells. The measured response is usually an average over the cell population. For example, a popular instrument used for ion channel assays is disclosed in U.S. Pat. No. 5,355,215. A typical assay consists of measuring the time-dependence of the fluorescence of an ion-sensitive dye, the fluorescence being a measure of the intra-cellular concentration of the ion of interest which changes as a consequence of the addition of a chemical compound. The dye is loaded into the population of cells disposed on the bottom of the well of a multiwell plate at a time prior to the measurement.

In general, the response of the cells is heterogeneous in both magnitude and time. This variability may obscure or prevent the observation of biological activity important to compound screening. Heterogeneity may result from either physiological or genetic differences in cells, or from experimental sources. A method that mitigates, compensates for, or even utilizes the variations would enhance the value of cell-based assays in the characterization of the pharmacological activity of chemical compounds.

Quantification of the response of individual cells circumvents the problems posed by the non-uniformity of that response of a population of cells. Consider the case where a minor fraction of the population responds to the stimulus. A device that measures the average response will have less sensitivity than one determining individual cellular response. However, analysis of the responses of individual cells will be time-consuming in the case of populations of large cell count.

The cell cycle is of key importance to many areas of drug discovery. On the one hand this fundamental process provides the opportunity to discover new targets for anticancer agents and improved chemotherapeutics, but on the other hand drugs and targets in other therapeutic areas must be tested for undesirable effects on the cell cycle. Historically, a wide range of techniques have been developed to study the cell cycle both as a global biochemical process and at the molecular level.

Known methods include those that produce data describing the proliferative activity of a cell population.

Measuring the incorporation of $[^{14}C]$- or $[^{3}H]$-thymidine (Regan, J. D. and Chu, E. H. (1966) "A convenient method for assay of DNA synthesis in synchronized human cell cultures" J. Cell Biol. 28, 139-143) by scintillation counting was one of the earliest methods of determining cell proliferation, and is still widely used today. More recent developments (Graves, R. et al. (1997) "Noninvasive, real-time method for the examination of thymidine uptake events—application of the method to V-79 cell synchrony studies" Anal. Biochem. 248, 251-257) have allowed thymidine incorporation to be measured in a homogeneous microplate assay format.

Several non-radioactive alternatives to thymidine incorporation assays have been developed. These include enzyme-linked immunosorbent assay (ELISA) nucleotide bromo-deoxyuridine (BrdU) (Perros, P. and Weightman, D. R. (1991) "Measurement of cell proliferation by enzyme-linked immunosorbent assay (ELISA) using a monoclonal antibody to bromodeoxyuridine. Cell. Prolif. 24, 517-523; Wemme, H. et al. (1992) "Measurement of lymphocyte proliferation: critical analysis of radioactive and photometric methods" Immunobiology 185, 78-89) into replicating DNA, and staining of proliferation-specific antigens such as Ki-67 (Frahm, S. O. et al (1998) "Improved ELISA proliferation assay (EPA) for the detection of in vitro cell proliferation by a new Ki-67-antigen directed monoclonal antibody (Ki-S3)" J. Immunol. Methods 211, 43-50).

Colourimetric methods based on substrate conversion (Mosmann, T. (1983) "Rapid colourimetric assay for cellular growth and survival: application to proliferation and cytotoxicity assays" J. Immunol. Methods 65, 55-63; Roehm, N. W. et al. (1991) "An improved colourimetric assay for cell proliferation and viability utilizing the tetrazolium sal XTT" J. Immunol. Methods 142, 257-265) by mitochondrial and other cellular enzymes are also used to measure cell growth. Although these assays are often referred to as cell-proliferation assays, strictly speaking they are cell-mass assays. Unlike measuring thymidine or BrdU incorporation, these assays do not provide any inherent measure of cell cycle progression, and give only a measure of cell mass ie. increase in cell number, relative to another population.

Other methods for measuring cell proliferation (i.e. increasing cell numbers) have been reported based on measuring electrical impedance (Upadhyay, P. and Bhaskar, S. (2000) "Real time monitoring of lymphocyte proliferation by an impedance method" J. Immunol. Methods 244, 133-137), dissolved oxygen (Wodnicka, M. et al (2000) "Novel fluorescent technology platform for high throughput cytotoxicity and proliferation assays" J. Biomol. Screen. 5, 141-152) and others. However, as for the colourimetric assays discussed above, these do not directly report cell cycle parameters and have not been widely adopted.

All of the above methods provide data on the overall proliferation within a cell population under examination, but do not identify the status of individual cells. Adaptation of these assays to imaging, for example by micro-autoradiography of $[^{3}H]$- or $[^{14}C]$-thymidine incorporation (Dormer, P. (1981) "Quantitative carbon-14 autoradiography at the cellular level: principles and application for cell kinetic studies" Histochem. J. 13, 161-171) or by immunocytochemical or immunofluorescence detection of BrdU (Dolbeare, F. (1995) "Bromodeoxyuridine: a diagnostic tool in biology and medicine, Part I: historical perspectives, histochemical methods and cell kinetics" Histochem. J. 27, 339-369) permits identification of cells that have traversed S phase, but does not yield information on the cell cycle position of other cells under analysis.

To determine the cell cycle status of all cells in a population it is a prerequisite that the analytical technique can resolve at least to the level of a single cell. Of the two qualifying techniques available, flow cytometry and microscopy, flow cytometry has become firmly established as the standard method for analysing cell cycle distribution.

The DNA content of cell nuclei varies through the cell cycle in a predictable fashion—cells in G2 or M have twice the DNA content of cells in G1, and cells undergoing DNA synthesis in S phase have an intermediate amount of DNA. Consequently, staining of cellular DNA with propidium iodide (Nairn, R. C. and Rolland, J. M. (1980) "Fluorescent probes to detect lymphocyte activation" Clin. Exp. Immunol. 39, 1-13) or other fluorescent dyes (Smith, P. J. et al (2000) "Characteristics of a novel deep red/infrared fluorescent cell-permeant DNA probe, DRAQ5, in intact human cells analyzed by flow cytometry, confocal and multiphoton microscopy" Cytometry 40, 280-291) that are compatible with live cells, followed by flow cytometry permits measurement of the relative proportion of cells in G1, S and G2/M phases. However, analysis by propidium iodide staining and flow cytometry is necessarily destructive and hence requires multiple samples to study cell cycle progression, which can become rate limiting where many hundreds of samples are to be analysed. In addition, flow cytometry does not yield fine resolution of cell cycle position in G2/M as the DNA content is the same in all cells.

A combination of DNA staining with pulsed BrdU incorporation can be used to resolve the cell cycle position further (Dolbeare, F. et al. (1983) "Flow cytometric measurement of total DNA content and incorporated bromodeoxyuridine" Proc. Natl. Acad. Sci. U.S.A. 80, 5573-5577). Dual-parameter analysis of DNA staining and/or BrdU incorporation can also be used with antibodies to cell-surface markers to profile cell cycle distribution in a defined subpopulation of cells (Mehta, B. A. and Maino, V. C. (1997) "Simultaneous detection of DNA synthesis and cytokine production in staphylococcal enterotoxin B activated CD4+T lymphocytes by flow cytometry" J. Immunol. Methods 208, 49-59; see also Johannisson, A. et al. (1995) "Activation markers and cell proliferation as indicators of toxicity: a flow cytometric approach" Cell Biol. Toxicol. 11, 355-366; see also Penit, C. and Vasseur, F. (1993) "Phenotype analysis of cycling and postcycling thymocytes: evaluation of detection methods for BrdUrd and surface proteins" Cytometry 14, 757-763).

Although to date flow cytometry has remained the dominant method for analysing the cell cycle, many of the above techniques have also been applied to microscopic analyses (Gorczyca, W. et al. (1996) "Laser scanning cytometer (LSC) analysis of fraction of labeled mitoses (FLM)" Cell Prolif. 29, 539-547; Clatch, R. J. and Foreman, J. R. (1998) "Five-colour immunophenotyping plus DNA content, analysis by laser scanning cytometry" Cytometry 34, 36-38).

The techniques described above all provide information in various forms from a single point in time (e.g. propidium iodide staining for DNA content) or integrated over a period of time (e.g. thymidine or BrdU incorporation). One further technique, cell-division tracking (Nordon, R. E. et al. (1999) "Analysis of growth kinetics by division tracking" Immunol. Cell Biol. 77, 523-529; Lyons, A. B. (1999) "Divided we stand: tracking cell proliferation with carboxyfluorescein diacetate succinimidyl ester" Immunol. Cell. Biol. 77, 509-515), allows the replicative history of a cell population to be analysed. In this method cells are loaded with a fluorescent dye such as carboxy-fluorescein diacetate succinimidyl ester (CFSE), which is partitioned between daughter cells at each successive round of cell division with a twofold reduction in fluorescence. Subsequent analysis of cell fluorescence by flow cytometry reveals the number of cell divisions undergone by each cell in the population. This technique has also been used in multi-parameter analyses combined with BrdU and proliferation-marker staining (Hasbold, J. and Hodgkin, P. D. (2000) "Flow cytometric cell division tracking using nuclei" Cytometry 40, 230-237).

International patent application WO 01/11341 describes a method for the automated measurement of the mitotic index of cells using fluorescence imaging. The technique involves immunoflourescence which reports specifically on mitotic cells by signals emitted from the cell nuclei, dependent upon the phosphorylation of histone H3. A mitotic index is determined by detecting the number of mitotic cells compared with the number of nuclei detected in a separate fluorescence channel. The technique involves simply counting cells having a signal above a given threshold, and is unsuited for the detection of cell cycle phases other than mitosis. Furthermore, the signal thresholds have to be predetermined, or entered by an operator.

The application of GFP and imaging techniques to cell cycle analysis has enabled significant advances to be made in understanding the timing of the molecular events that control the cell cycle. Fusing. GFP with key cell-cycle-control proteins has provided significant insights into the molecular organisation behind the cell cycle (see (Raff, J. W. et al (2002) "The roles of Fzy/Cdc20 and Fzr/Cdh1 in regulating the destruction of cyclin B in space and time" J. Cell Biol. 157, 1139-1149; Zeng, Y. et al. (2000) "Minimal requirements for the nuclear localization of p27(Kip1), a cyclin-dependent kinase inhibitor" Biochem. Biophys. Res. Commun. 274, 37-42; Huang, J. and Raff. J. W. (1999) "The disappearance of cyclin B at the end of mitosis is regulated spatially in *Drosophila cells*" EMBO J. 18, 2184-2195; Weingartner, M. et al. (2001) "Dynamic recruitment of Cdc2 to specific microtubule structures during mitosis" Plant Cell 13, 1929-1943; Arnaud, L. et al. (1998) "GFP tagging reveals human Polo-like kinase 1 at the kinetochore/centromere region of mitotic chromosomes" Chromosoma 107, 424-429) and other cellular components (Kanda, T. et al. (1998) "Histone-GFP fusion protein enables sensitive analysis of chromosome dynamics in living mammalian cells" Curr. Biol. 8, 377-385; Reits, E. A. et al. (1997) "Dynamics of proteasome distribution in living cells" EMBO J. 16, 6087-6094; Tatebe, H. et al. (2001) "Fission yeast living mitosis represented by GFP-tagged gene products" Micron 32, 67-74)). However, although these specialised approaches provide valuable data on the mechanisms and components involved, they are not generic methods for monitoring the cell cycle.

Another purpose of cell cycle analysis (and for example cyclin cell lines) is to first classify the cells in the population, then to perform analysis of other parameters on each subpopulation separately using reporters in other channels. Cells at different stages will respond differently to different compounds (e.g. cell surface receptors cannot be activated in mitotic cells.)

SUMMARY OF THE INVENTION

In accordance with one aspect of the present invention, there is provided a method of classifying cells into subpopulations using cell classifying data, the method comprising: receiving image data; analyzing said image data to identify object areas in the image data; analyzing said image data, on the basis of said identified object areas, to determine, for at least one selected first cell, one or more measurements; deriving a first parameter set for the first cell, the first parameter set comprising at least one of said one or more measurements; classifying a first set of cells, the process of classifying the first set of cells including classifying the first cell into a subpopulation and storing first identifying data indicating the subpopulation into which the first cell has been classified; deriving cell classifying data for use in classifying a second set cells into subpopulations from the first parameter set and the first identifying data, and classifying a second set of cells into subpopulations on the basis of one or more measurements taken for cells in the second set of cells, by use of the cell classifying data.

The present invention provides a cell classification method that 'learns' from previous classifications, in a training process. The process of learning to classify by the analysis of data relating to previously classified examples may be by means of a process termed 'supervised learning', and as such the present invention provides a robust method of supervised learning for the purposes of cellular analysis. Cell classifying data, which may alternatively be referred to as training data, is derived from a parameter set and associated identifying data. The parameter set includes at least one measurement relating to a cell. The object area may relate correspond to an entire cell, an area corresponding to or within the nucleus, an area corresponding to or within the cytoplasm, or other object areas corresponding to or within subcellular components. Examples of measurements include:

an average signal intensity within an identified object area;

a fraction of pixels that deviate more than a given amount from an average signal intensity within an identified object area;

a number of pixels with a signal intensity below a given threshold within an identified object area;

a ratio between major and minor axes of an elliptical outline corresponding to an identified object area;

a maximum width of an identified object area;

an average width of an identified object area;

signal texture within an identified object area;

margination in an identified object area.

In an embodiment, the measurement(s) may be calculated automatically using a set of image analysis routines. The measurements for each object area may then be stored in memory in association with identification data, to build up a database of classifying data, which can later be applied with minimal user intervention to further sets of cells. High-throughput automated cell classification can thereby be achieved.

A method according to the present invention may derive cell classifying data based on parameter sets including any measurement determined from the image data. In this way, cell classifying data may be derived from image data that includes but is not limited to the luminescence data. A parameter set may be derived from the one or more measurements taken for the second set of cells.

A method according to the present invention may be used to classify cells into subpopulations according to cell morphology. For example, the identifying data may be neurite formation/outgrowth or may classify the cell according to other criteria.

A method according to the present invention may be used to classify cells into subpopulations according to receptor binding. For example, the identifying data may be granule/vesicle formation or colour change (e.g. in the presence of specific dyes such as CypHer™5 from Amersham Biosciences) or may classify the cell according to other criteria.

A method according to the present invention may be used to classify cells into subpopulations according to cell cycle phase. The identifying data may be a cell cycle phase classification (e.g. 'prophase', 'metaphase', 'anaphase', 'telophase', 'G2', 'S', 'G2') or may classify the cell according to other criteria.

A method according to the present invention may take any measurement of the second set of cells from the image data without user intervention and as such will not require an operator to input any threshold or specify any measurement value relating to the second set of cells. The cell classifying data derived from the identifying data and the parameter set will therefore be derived from objective and accurate measurement data, facilitating accurate classification of further sets of cells.

Use of the cell classifying data to classify a second set of cells may include comparing the measurements for cells in the second set with the cell cycle classifying data derived from classification of the first set of cells. For example, if a cell in the first set is classified as being in prophase, and the parameter set for that cell includes a measurement of reporter luminescence having a value x, a cell in the second set which is determined to also have a reporter luminescence value sufficiently similar to x may be classified as also being in prophase. In this way, the derivation of the cell classifying data and the application of the data to a second set of cells allows automated classification of the second set of cells.

The use of the cell classifying data to classify a second set of cells may include calculating a statistical likelihood for each cell in second set of being a member of a classified group. For example, the value of a measurement taken for a cell in the second set may be compared with the analogous measurement in the parameter sets of classified cells and, if no exact match of the value is found, the nearest match is calculated, and the cell in the second set classified according to the nearest match. Several measurements may be taken and weighted in statistical importance when compared with the parameter sets of classified cells.

In embodiments where n measurements are taken from the cell image data, the parameter set may be represented as a feature vector, in an n-dimensional feature space. The representation of the parameter set as a feature vector in a feature space allows a number of classification techniques to be employed, and is described in more detail below.

Further features and advantages of the invention will become apparent from the following description of preferred embodiments of the invention, given by way of example only, which is made with reference to the accompanying drawings.

DETAILED DESCRIPTION OF THE INVENTION

The present invention is useful for identifying pharmacological agents for the treatment of disease. It provides a potentially automated, high throughput method for conducting a wide variety of biological assays where one or more markers, including luminescent markers, are employed to measure a biological response. Several markers may be used in conjunction to derive a variety of measurements, and the measurements may be determined automatically to ensure accuracy. Such assays can be conducted on chemical compounds or any molecule of biological interest, including but not limited to drug candidates, such as those found in combinatorial libraries, allowing high throughput screening of chemical compounds of biological interest.

The techniques of the present invention may be used in assays in which data are acquired on individual cells, on a cellular or sub-cellular level, sufficiently rapidly so as to permit the acquisition of such data on a sufficient number of cells to constitute a statistically meaningful sample of the cell population.

These assays may make use of any known fluorophore or fluorescent label including but not limited to fluorescein, rhodamine, Texas Red, Amersham Corp. stains Cy3, Cy5, Cy5.5 and Cy7, Hoechst's nuclear stains and Coumarin stains. (See Haugland, R. P., Handbook of Fluorescent Probes and Research Chemicals 6$^{th}$ Ed., 1996, Molecular Probes, Inc., Eugene, Oreg.)

Figure 1:
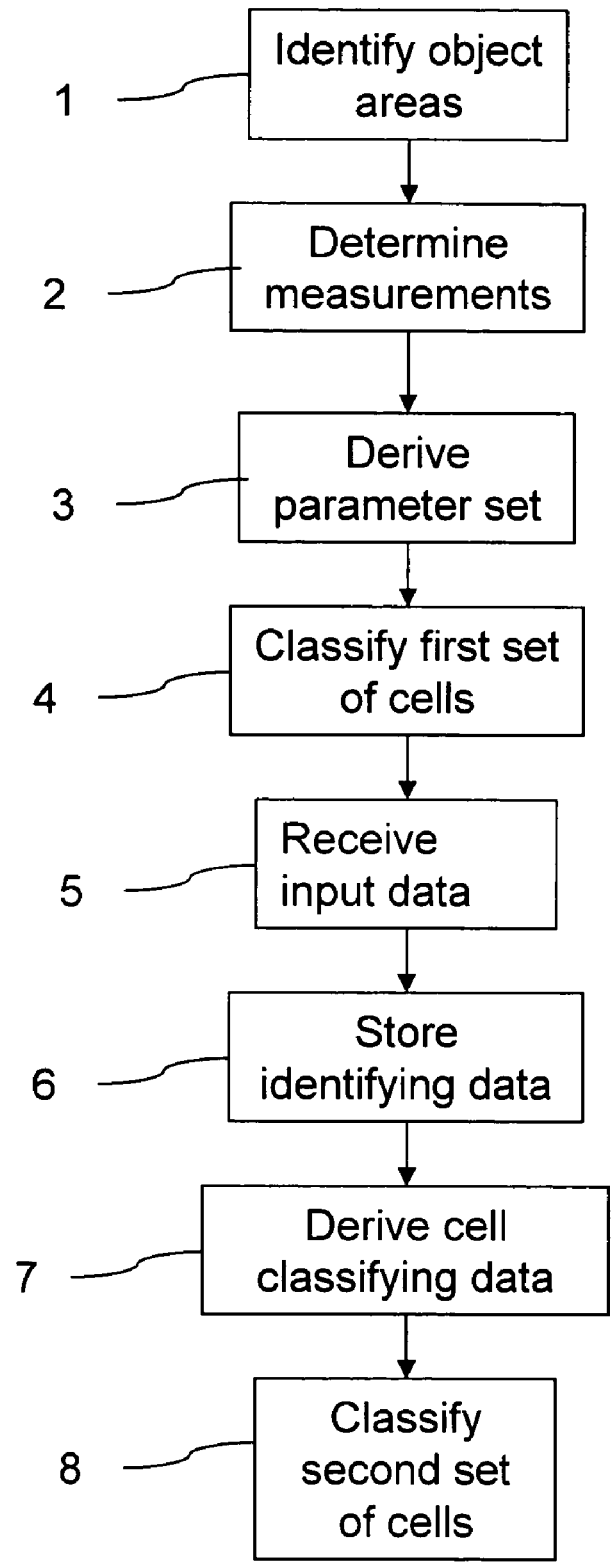
FIG. 1 is a flow diagram showing a method of cell classification according to an embodiment of the invention.

FIG. 1 is a flow diagram illustrating an embodiment of the invention. Image data from a first cell population is received by an imaging device which incorporates a data processing system. The image data is analysed by the data processing system in step 1 to derive object areas which correspond to cells and the areas within cells, specifically the nucleus and cytoplasm.

In step 2, measurements are taken from the image data. These measurements may relate to the intensity, morphology and dimensions of the cells represented in the image data. The measurements are stored in the memory of the data processing system.

At step 3, the measurements for each cell identified from the image data are grouped together in a parameter set, stored in the memory of the data processing system. Each cell identified in the image data is assigned its own parameter set.

At step 4, a user classifies cells represented in the image data. This may be done via a known graphical user interface attached to the data processing system. The data resulting from the user classifying cells is received by the data processing system at step 5. The identifying data for each cell is saved in association with that cell's parameter set in the memory of the data processing system in step 6, to derive classifying data at step 7. The identifying data allots each cell to a subpopulation based on features in the cell image data.

In step 8, the classifying data is applied to a second set of cells. The second set of cells is analysed by the imaging device, divided into object areas, and measurements are taken in a manner similar to steps 1 and 2. The measurements are then analysed and the second set of cells are divided into subpopulations, on the basis of the measurements taken for cells in the second set of cells, by use of the cell classifying data.

A detailed description of the steps shown in FIG. 1 follows.

Figure 2:
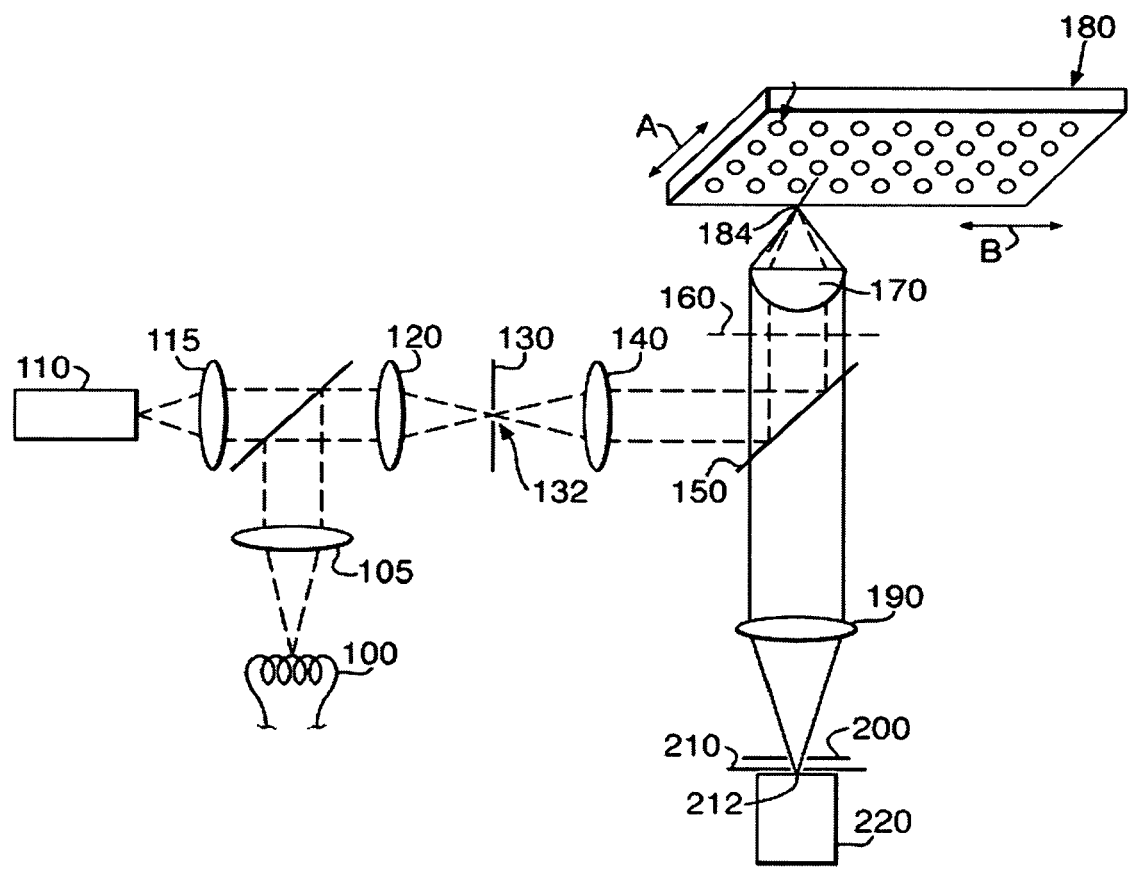
FIG. 2 is a schematic view of a first embodiment of a line-scan confocal microscope used to image samples according to the present invention.

FIG. 2 shows a first embodiment of the present invention, where the imaging device used is a microscope. The microscope comprises a source 100 or 110 of electromagnetic radiation for example, in the optical range, 350-750 nm, a cylindrical lens 120, a first slit mask 130, a first relay lens 140, a dichroic mirror 150, an objective lens 170, a microtiter plate 180 containing a two-dimensional array of sample wells 182, a tube lens 190, a filter 200, a second slit mask 210 and a detector 220. These elements are arranged along optical axis OA with slit apertures 132, 212 in masks 130, 210 extending perpendicular to the plane of FIG. 2. The focal lengths of lenses 140, 170 and 190 and the spacings between these lenses as well as the spacings between mask 130 and lens 140, between objective lens 170 and microtiter plate 180 and between lens 190 and mask 210 are such as to provide a confocal microscope. In this embodiment, electromagnetic radiation from a lamp 100 or a laser 110 is focused to a line using a cylindrical lens 120. The shape of the line is optimized by a first slit mask 130. The slit mask 130 is depicted in an image plane of the optical system that is in a plane conjugate to the object plane. The illumination stripe formed by the aperture 132 in the slit mask 130 is relayed by lens 140, dichroic mirror 150 and objective lens 170 onto a microtiter plate 180 which contains a two-dimensional array of sample wells 182. For convenience of illustration, the optical elements of FIG. 2 are depicted in cross-section and the well plate in perspective. The projection of the line of illumination onto well plate 180 is depicted by line 184 and is also understood to be perpendicular to the plane of FIG. 2. As indicated by arrows A and B, well plate 180 may be moved in two dimensions (X, Y) parallel to the dimensions of the array by means not shown.

In an alternative embodiment, the slit mask 130 resides in a Fourier plane of the optical system that is in a plane conjugate to the objective back focal plane (BFP) 160. In this case the aperture 132 lies in the plane of the figure, the lens 140 relays the illumination stripe formed by the aperture 132 onto the back focal plane 160 of the objective 170 which transforms it into a line 184 in the object plane perpendicular to the plane of FIG. 2.

In an additional alternative embodiment the slit mask 130 is removed entirely. According to this embodiment, the illumination source is the laser 110, the light from which is focused into the back focal plane 160 of the objective 170. This can be accomplished by the combination of the cylindrical lens 120 and the spherical lens 140 as shown in FIG. 2, or the illumination can be focused directly into the plane 160 by the cylindrical lens 120.

An image of the sample area, for example a sample in a sample well 182, is obtained by projecting the line of illumination onto a plane within the sample, imaging the fluorescence emission therefrom onto a detector 220 and moving the plate 180 in a direction perpendicular to the line of illumination, synchronously with the reading of the detector 220. In the embodiment depicted in FIG. 2, the fluorescence emission is collected by the objective lens 170, projected through the dichroic beamsplitter 150, and imaged by lens 190 through filters 200 and a second slit mask 210 onto a detector 220, such as is appropriate to a confocal imaging system having an infinity-corrected objective lens 170. The dichroic beamsplitter 150 and filter 200 preferentially block light at the illumination wavelength. The detector 220 illustratively is a camera and may be either one dimensional or two dimensional. If a one dimensional detector is used, slit mask 210 is not needed. The illumination, detection and translation procedures are continued until the prescribed area has been imaged. Mechanical motion is simplified if the sample is translated at a continuous rate. Continuous motion is most useful if the camera read-time is small compared to the exposure-time. In a preferred embodiment, the camera is read continuously. The displacement d of the sample during the combined exposure-time and read-time may be greater than or less than the width of the illumination line W, exemplarily $0.5W \leq d \leq 5W$. All of the wells of a multiwell plate can be imaged in a similar manner.

Alternatively, the microscope can be configured to focus a line of illumination across a number of adjacent wells, limited primarily by the field-of-view of the optical system. Finally, more than one microscope can be used simultaneously.

The size and shape of the illumination stripe 184 is determined by the width and length of the Fourier transform stripe in the objective lens back focal plane 160. For example, the length of the line 184 is determined by the width of the line in 160 and conversely the width in 184 is determined by the length in 160. For diffraction-limited performance, the length of the illumination stripe at 160 is chosen to overfill the objective back aperture. It will be evident to one skilled in the art that the size and shape of the illumination stripe 184 can be controlled by the combination of the focal length of the cylindrical lens 120 and the beam size at 120, that is by the effective numerical aperture in each dimension, within the restrictions imposed by aberrations in the objective, and the objective field of view.

The dimensions of the line of illumination 184 are chosen to optimize the signal to noise ratio. Consequently, they are sample dependent. Depending on the assay, the resolution may be varied between diffraction-limited, i.e., less than 0.5 µm, and approximately 5 µm. The beam length is preferably determined by the objective field of view, exemplarily between 0.5 and 1.5 mm. A Nikon ELWD, 0.6 NA, 10× objective, for example, has a field of view of approximately 0.75 mm. The diffraction-limited resolution for 633 nm radiation with this objective is approximately 0.6 µM or approximately 1100 resolution elements.

The effective depth resolution is determined principally by the width of aperture 212 in slit mask 210 or the width of the one dimensional detector and the image magnification created by the combination of the objective lens 170 and lens 190. The best depth resolution of a confocal microscope approaches 1 µm. In the present application, a depth resolution of 5-10 µm may be sufficient or even advantageous.

For example, when the sample of interest, such as a live cell, contains insufficient fluorophores in a diffraction-limited volume to permit an adequate signal-to-noise image in a sufficiently brief image-acquisition time, it is advantageous to illuminate and collect the emission from a larger than diffraction-limited volume. A similar situation prevails in the case of video-rate kinetics studies of transient events such as ion-channel openings. Practically, this is accomplished by underfilling the back aperture of the objective lens, which is equivalent to increasing the diameter of the illumination aperture. The effective numerical aperture ("NA") of the illumination is less than the NA of the objective. The fluorescence emission is, however, collected with the full NA of the objective lens. The width of aperture 212 must be increased so as to detect emission from the larger illumination volume. At an aperture width a few times larger than the diffraction limit, geometrical optics provides an adequate approximation for the size of the detection-volume element:

Lateral Width: $a_d = d_d/M$,

Axial Width: $z_d = \sqrt{3} A_d / \tan \alpha$, where M is the magnification, $d_d$ is the width of aperture 212 and α is the half-angle subtended by the objective 170. It is an important part of the present invention that the illumination aperture 132 or its equivalent in the embodiment having no aperture and the detection aperture 212 be independently controllable.

Multi-Wavelength Configuration

An embodiment enabling multi-wavelength fluorescence imaging is preferred for certain types of assays. In this way, image data can be generated for the same area being imaged in each of a plurality of different colour channels simultaneously.

Figure 3A:
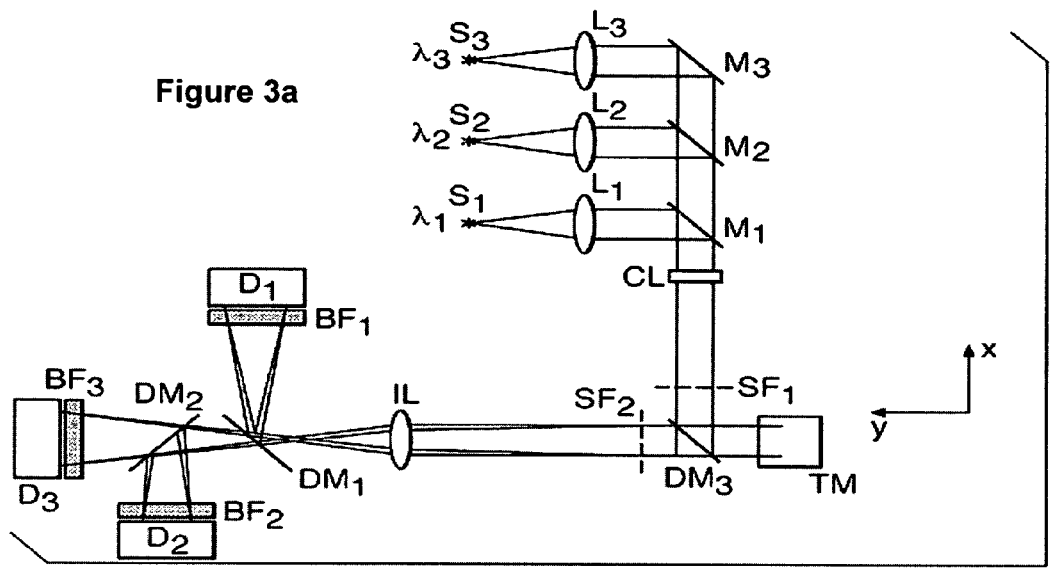
FIGS. 3A and 3B are, respectively, a top view and a side view of the ray path of a multicolour embodiment of the present invention, without a scanning mirror.
Figure 3B:
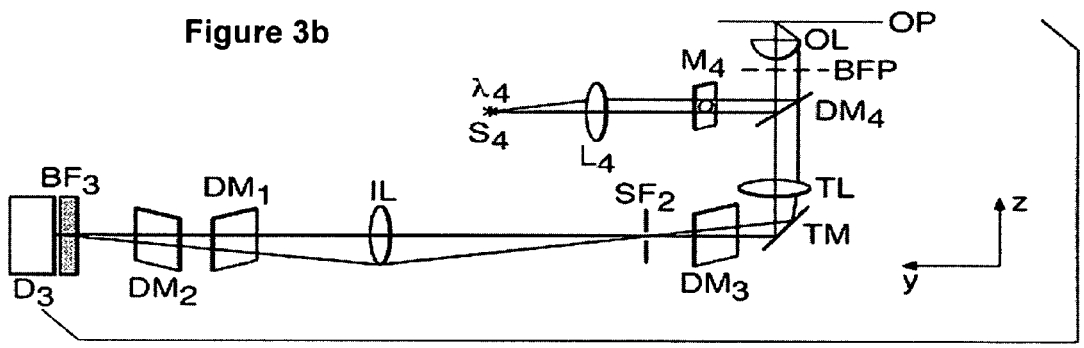

The number of independent wavelengths or colours will depend on the specific assay being performed. In one embodiment three illumination wavelengths are used. FIGS. 3A and 3B depict the ray paths in a three-colour line-scan confocal imaging system, from a top view and a side view respectively. In general, the system comprises several sources $S_n$ of electromagnetic radiation, collimating lenses $L_n$, and mirrors $M_n$ for producing a collimated beam that is focused by cylindrical lines CL into an elongated beam at first spatial filter $SF_1$, a confocal microscope between first spatial filter $SF_1$, and second spatial filter $SF_2$ and an imaging lens IL, beamsplitters $DM_1$ and $DM_2$ and detectors $D_n$ for separating and detecting the different wavelength components of fluorescent radiation from the sample. Spatial filters SF, and $SF_1$ and $SF_2$ preferably are slit masks.

In particular, FIG. 3A depicts sources, $S_1$, $S_2$ and $S_3$, for colours $\lambda_1$, $\lambda_2$ and $\lambda_3$, and lenses $L_1$, $L_2$ and $L_3$ that collimate the light from the respective sources. Lenses $L_1$, $L_2$ and $L_3$, preferably are adjusted to compensate for any chromaticity of the other lenses in the system. Mirrors $M_1$, $M_2$ and $M_3$ are used to combine the illumination colours from sources $S_n$. The mirrors $M_2$ and $M_1$ are partially transmitting, partially reflecting and preferentially dichroic. $M_2$, for example, should preferentially transmit $\lambda_3$, and preferentially reflect $\lambda_2$. It is thus preferential that $\lambda_3$ be greater than $\lambda_2$.

Operation of the microscope in a confocal mode requires that the combined excitation beams from sources $S_n$ be focused to a "line", or an highly eccentric ellipse, in the object plane OP. As discussed in connection to FIG. 2 above, a variety of configurations may be used to accomplish this. In the embodiment depicted in FIG. 3A, the combined illumination beams are focused by cylindrical lens CL into an elongated ellipse that is coincident with the slit in the spatial filter $SF_1$. As drawn in FIGS. 3A and 3B, the slit mask $SF_1$ resides in an image plane of the system, aligned perpendicular to the propagation of the illumination light and with its long axis in the plane of the page of FIG. 3A. The lenses TL and OL relay the illumination line from the plane containing $SF_1$ to the object plane OP. A turning mirror, TM, is for convenience. In another embodiment, $DM_3$ is between TL and OL and CL focuses the illumination light directly into the BFP. Other embodiments will be evident to one skilled in the art.

Referring to FIG. 3B, the light emitted by the sample and collected by the objective lens, OL, is imaged by the tube lens, TL, onto the spatial filter, $SF_2$. $SF_2$ is preferentially a slit aligned so as to extend perpendicular to the plane of the page. Thus, the light passed by filter $SF_2$ is substantially a line of illumination. $SF_2$ may be placed in the primary image plane or any plane conjugate thereto. $DM_3$ is partially reflecting, partially transmitting and preferably "multichroic". Multi-wavelength "dichroic" mirrors, or "multichroic" mirrors can be obtained that preferentially reflect certain wavelength bands and preferentially transmit others.

Here, $\delta\lambda_1$ will be defined to be the fluorescence emission excited by $\lambda_1$. This will, in general, be a distribution of wavelengths somewhat longer than $\lambda_1$. $\delta\lambda_2$ and $\delta\lambda_3$ are defined analogously. $DM_3$ preferentially reflects $\lambda_n$, and preferentially transmits $\delta\lambda_n$, n=1, 2, 3. The light transmitted by $SF_2$ is imaged onto the detection devices, which reside in planes conjugate to the primary image plane. In FIG. 3A, an image of the spatial filter $SF_2$ is created by lens IL on all three detectors, $D_n$. This embodiment is preferred in applications requiring near-perfect registry between the images generated by the respective detectors. In another embodiment, individual lenses $IL_n$, are associated with the detection devices, the lens pairs IL and $IL_n$ serving to relay the image of the spatial filter $SF_2$ onto the respective detectors $D_n$. The light is split among the detectors by mirrors $DM_1$ and $DM_2$. The mirrors are partially transmitting, partially reflecting, and preferentially dichroic. $DM_1$ preferentially reflects $\delta\lambda_1$ and preferentially transmits $\delta\lambda_2$ and $\delta\lambda_3$. The blocking filter, $BF_1$, preferentially transmits $\delta\lambda_1$ effectively blocking all other wavelengths present. $DM_2$ preferentially reflects $\delta\lambda_2$ and preferentially transmits $\delta\lambda_3$. The blocking filters, $BF_2$ and $BF_3$, preferentially transmit $\delta\lambda_2$ and $\delta\lambda_3$ respectively, effectively blocking all other wavelengths present.

Scanning Mirror Configuration

In some embodiments of this invention, rapid data acquisition is provided by framing images at video rates. Video-rate imaging allows up to 30 or even 60 frames per second. In the present use, it is intended to connote frame rates with an order-of-magnitude of 30 Hz. In a preferred embodiment, video-rate imaging is achieved by illuminating along one dimension of the sample plane and scanning the illumination beam in the direction perpendicular thereto so as to effect a relative translation of the illumination and sample. The scanning stage is generally massive and so cannot be moved sufficiently rapidly.

Figure 4A:
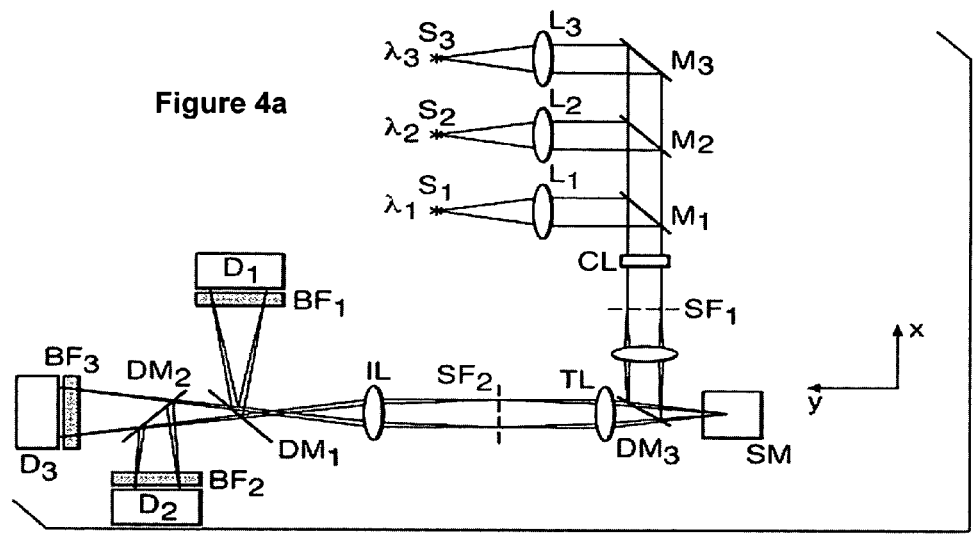
FIGS. 4A and 4B are, respectively, a top view and a side view of the ray path of the multicolour embodiment of the present invention with the scanning mirror.
Figure 4B:
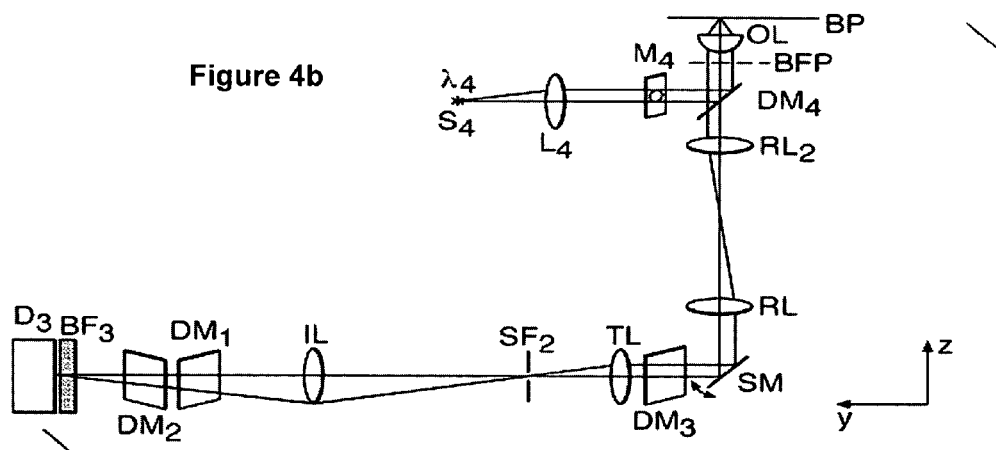
Figure 4C:
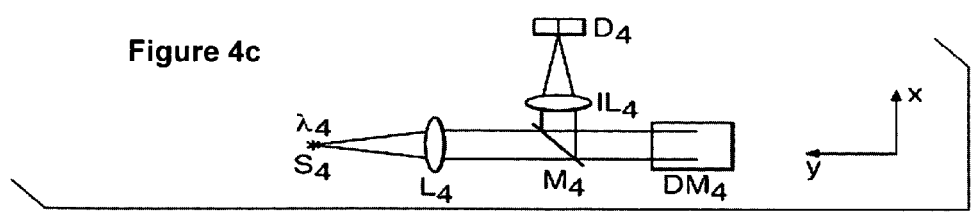
FIG. 4C is a top view of the ray path of the single beam autofocus.

FIGS. 4A, 4B and 4C depict an embodiment of the invention utilizing a scanning mirror, SM. The mirror is advantageously placed in a plane conjugate to the objective back focal plane (BFP): A rotation in the BFP (or a plane conjugate thereto) effects a translation in the object plane (OP) and its conjugate planes. The full scan range of SM need only be a few degrees for typical values of the focal lengths of the lenses $RL_1$ and $RL_2$. As shown in FIGS. 4, 4B and 4C, this lens pair images the BFP onto the SM at a magnification of one, but a variety of magnifications can be advantageously used. The limiting factors to the image acquisition rate are the camera read-rate and the signal strength. In the imaging mode described above, data can be acquired continuously at the camera read-rate, exemplarily 1 MHz. With a scanning mirror, it is preferable to acquire data uni-directionally. The idealized scanning motion allowing one to acquire data continuously is the sawtooth. In practice, the combination of turn-around and return scan times will constitute ~⅓-⅔ of the scan period. Assuming 50% dead-time, a mirror oscillation frequency of 50 Hz and a pixel acquisition rate of 1 MHz, ~10,000 pixels would be acquired per frame at 50 frames per second, which is sufficient to define and track individual objects, such as cells, from frame to frame. $10^4$ pixels per image is, however, $10^2$-times fewer than was generally considered above. Depending on the application, it is advantageous to acquire relatively smaller images at high resolution, e.g. 50-μm×50-μm at 0.5-μm×0.5-μm pixelation, or relatively larger images at lower resolution, e.g. 200-μm×200-μm at 2-μm pixelation.

Autofocus

In preferred embodiments of the present invention, the sample lies in the object plane of an imaging system. Accordingly, an autofocus mechanism is used that maintains the portion of the sample in the field-of-view of the imaging system within the object plane of that system. The precision of planarity is determined by the depth-of-field of the system. In a preferred embodiment, the depth-of-field is approximately 10 μm and the field-of-view is approximately 1 $mm^2$.

The autofocus system operates with negligible delay, that is, the response time is short relative to the image acquisition-time, exemplarily 0.01-0.1 s. In addition, the autofocus light source is independent of the illumination light sources and the sample properties. Among other advantages, this configuration permits the position of the sample carrier along the optical axis of the imaging system to be determined independent of the position of the object plane.

Figure 3C:
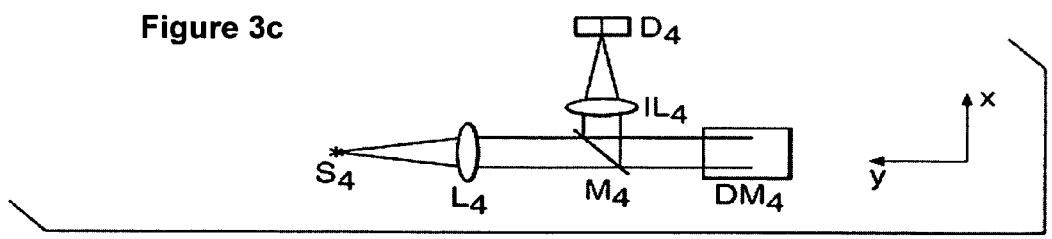
FIG. 3C is a top view of the ray path of a single beam autofocus.

Embodiments of single-beam autofocus are shown in FIG. 4C, where a separate light source, $S_4$ of wavelength $\lambda_4$, and detector $D_4$ are shown. The wavelength $\lambda_4$ is necessarily distinct from the sample fluorescence, and preferentially a wavelength that cannot excite appreciable fluorescence in the sample. Thus, $\lambda_4$ is preferentially in the near infrared, exemplarily 800-1000 nm. The partially transmitting, partially reflecting mirror, $DM_4$, is preferentially dichroic, reflecting $\lambda_4$ and transmitting $\lambda_n$ and $\delta\lambda_n$, n=1, 2, 3. Optically-based autofocus mechanisms suitable for the present application are known. For example, an astigmatic-lens-based system for the generation of a position error signal suitable for servo control is disclosed in *Applied Optics* 23 565-570 (1984). A focus error detection system utilizing a "skew beam" is disclosed in *SPIE* 200 73-78 (1979). The latter approach is readily implemented according to FIGS. 3C and 3C, where $D_4$ is a split detector.

For use with a microtiter plate having a sample residing on the well bottom, the servo loop must, however, be broken to move between wells. This can result in substantial time delays because of the need to refocus each time the illumination is moved to another well.

Figure 5:
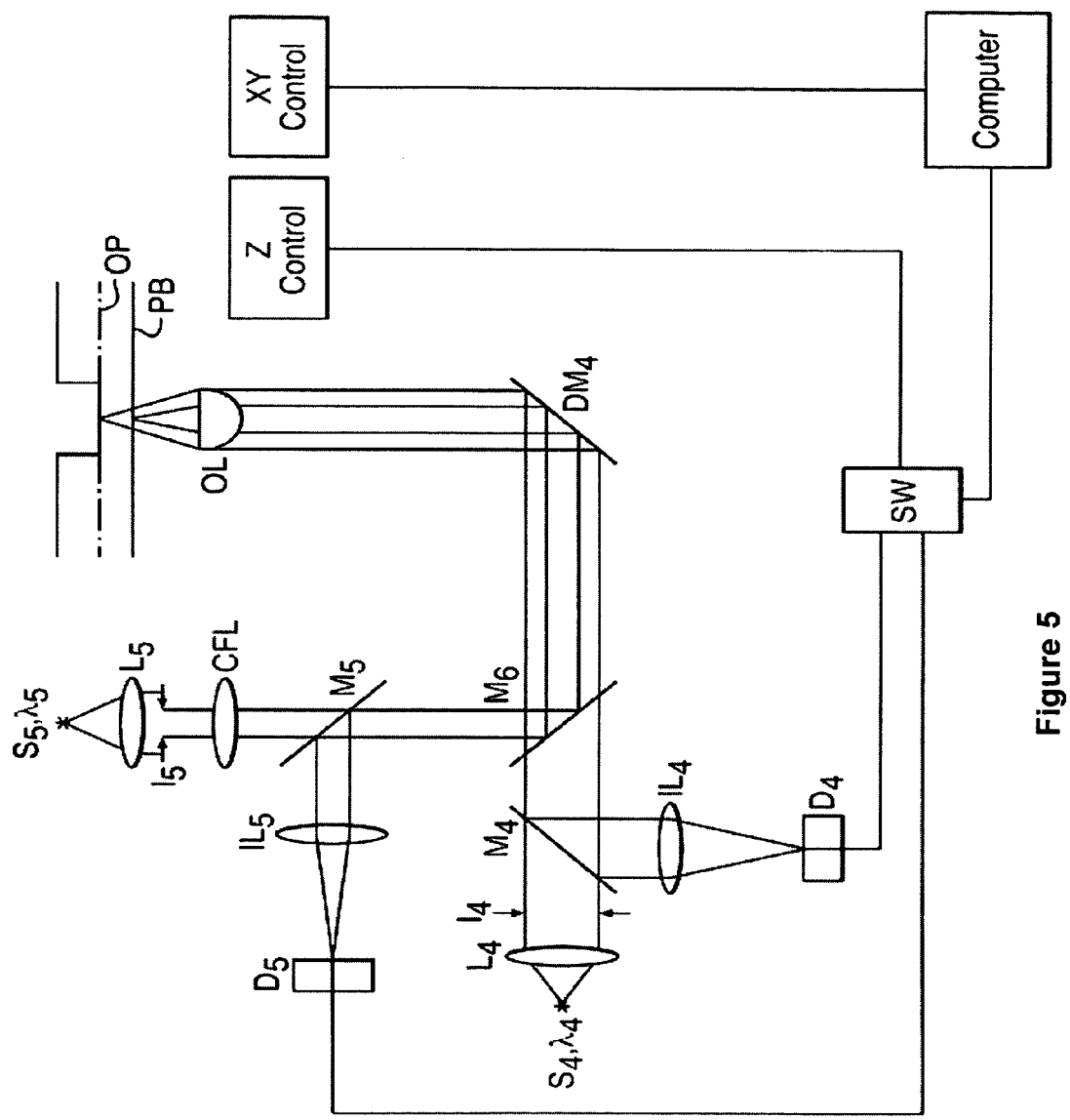
FIG. 5 is a side view of the two beam autofocus system.

Continuous closed-loop control of the relative position of the sample plane and the object plane is provided in a preferred embodiment of the present invention, depicted in FIG. 5. This system utilizes two independent beams of electromagnetic radiation. One, originating from $S_5$, is focused on the continuous surface, exemplarily the bottom of a microtiter plate. The other, originating from $S_4$, is focused on the discontinuous surface, exemplarily the well bottom of a microtiter plate. In one embodiment, the beams originating from $S_4$ and $S_5$ have wavelengths $\lambda_4$ and $\lambda_5$, respectively. $\lambda_4$ is collimated by $L_4$, apertured by iris $I_4$, and focused onto the discontinuous surface by the objective lens OL. $\lambda_5$ is collimated by $L_5$, apertured by iris $I_5$, and focused onto the continuous surface by the lens CFL in conjunction with the objective lens OL. The reflected light is focused onto the detectors $D_4$ and $D_5$ by the lenses $IL_4$ and $IL_5$, respectively. The partially transmitting, partially reflecting mirror, $DM_4$, is preferentially dichroic, reflecting $\lambda_4$ and $\lambda_5$ and transmitting $\lambda_n$ and $\delta\lambda_n$, n=1, 2, 3. The mirrors, $M_4$, $M_5$ and $M_6$, are partially transmitting partially reflecting. In the case that $\lambda_4$ and $\lambda_5$ are distinct, $M_6$ is preferentially dichroic.

According to the embodiment wherein the sample resides in a microtiter plate, $\lambda_4$ is focused onto the well bottom. The object plane can be offset from the well bottom by a variable distance. This is accomplished by adjusting $L_4$ or alternatively by an offset adjustment in the servo control loop. For convenience of description, it will be assumed that $\lambda_4$ focuses in the object plane.

The operation of the autofocus system is as follows. If the bottom of the sample well is not in the focal plane of objective lens OL, detector $D_4$ generates an error signal that is supplied through switch SW to the Z control. The Z control controls a motor (not shown) for moving the microtiter plate toward or away from the objective lens. Alternatively, the Z control could move the objective lens. If the bottom PB of the microtiter plate is not at the focal plane of the combination of the lens CFL and the objective lens OL, detector $D_5$ generates an error signal that is applied through switch SW to the Z control. An XY control controls a motor (not shown) for moving the microtiter plate in the object plane OP of lens OL.

As indicated, the entire scan is under computer control. An exemplary scan follows: At the completion of an image in a particular well, the computer operates SW to switch control of the servo mechanism from the error signal generated by $D_4$ to that generated by $D_5$; the computer then directs the XY control to move the plate to the next well, after which the servo is switched back to $D_4$.

The "coarse" focusing mechanism utilizing the signal from the bottom of the plate is used to maintain the position of the sample plane to within the well-to-well variations in the thickness of the plate bottom, so that the range over which the "fine" mechanism is required to search is minimized. If, for example, the diameter of the iris $I_5$ is 2 mm and $IL_5$ is 100 mm, then the image size on the detector will be ~100 $\lambda$m. Similarly, if the diameter of the iris $I_4$ is 0.5 mm and $IL_4$ is 100 mm, then the image size on the detector will be ~400 µm. The latter is chosen to be less sensitive so as to function as a "coarse" focus.

As with the single-beam embodiment described above, the wavelengths $\lambda_4$ and $\lambda_5$ are necessarily distinct from the sample fluorescence, and preferentially wavelengths that cannot excite appreciable fluorescence in the sample. Thus, $\lambda_4$ and $\lambda_5$ are preferentially in the near infrared, such as 800-1000 nm. In addition, the two wavelengths are preferably distinct, for example $\lambda_4$=830 nm, $\lambda_5$=980 nm.

In an alternative embodiment of two-beam autofocus, $\lambda_4$=$\lambda_5$ and the two beams may originate from the same source. Preferentially, the two beams are polarized perpendicular to one another and $M_6$ is a polarizing beamsplitter.

Pseudo-closed loop control is provided in the preferred embodiment of single-beam autofocus which operates as follows. At the end of a scan the computer operates SW to switch control to a sample-and-hold device which maintains the Z control output at a constant level while the plate is moved on to the next well after which SW is switched back to $D_4$.

Detection Devices

A detection device is used having manifold, independent detection elements in a plane conjugate to the object plane. As discussed above, line illumination is advantageous principally in applications requiring rapid imaging. The potential speed increase inherent in the parallelism of line illumination as compared to point illumination is, however, only realized if the imaging system is capable of detecting the light emitted from each point of the sample along the illumination line, simultaneously.

It is possible to place a charge-coupled device (CCD), or other camera, at the output of the prior art imaging systems described above (White et al., U.S. Pat. No. 5,452,125 and Brakenhoff and Visscher, *J. Microscopy* 171 17-26 (1993)). The resulting apparatus has three significant disadvantages compared to the present invention. One is the requirement of rescanning the image onto the two-dimensional detector, which adds unnecessary complexity to the apparatus. Another is the requirement of a full two-dimensional detector having sufficient quality over the 1000 pixel×1000 pixel array that typically constitutes the camera. The third disadvantage is the additional time required to read the full image from the two-dimensional device.

To avoid these disadvantages and optimize not only imaging speed, within the constraints of high-sensitivity and low-noise detection, but also throughput, a continuous-read line-camera is used and in a preferred embodiment a rectangular CCD is used as a line-camera. Both embodiments have no dead-time between lines within an image or between images. An additional advantage is that a larger effective field-of-view is achievable in the stage-scanning embodiment, discussed below.

The properties required of the detection device can be further clarified by considering the following preferred embodiment. The resolution limit of the objective lens is <1 µm, typically ~0.5 µm, and the detector comprises an array of ~1000 independent elements. Resolution, field-of-view (FOV) and image acquisition-rate are not independent variables, necessitating compromise among these performance parameters. In general, the magnification of the optical system is set so as to image as large a FOV as possible without sacrificing resolution. For example, a ~1 mm field-of-view could be imaged onto a 1000-element array at 1-μm pixelation. If the detection elements are 20-μm square, then the system magnification would be set to 20×. Note that this will not result in 1-μm resolution. Pixelation is not equivalent to resolution. If, for example, the inherent resolution limit of the objective lens is 0.5 μm and each 0.5 μm×0.5 μm region in the object plane is mapped onto a pixel, the true resolution of the resulting digital image is not 0.5 μm. To achieve true 0.5-μm resolution, the pixelation would need to correspond to a region ~0.2 μm×0.2 μm in the object plane. In one preferred embodiment, the magnification of the imaging system is set to achieve the true resolution of the optics.

Figure 6A:
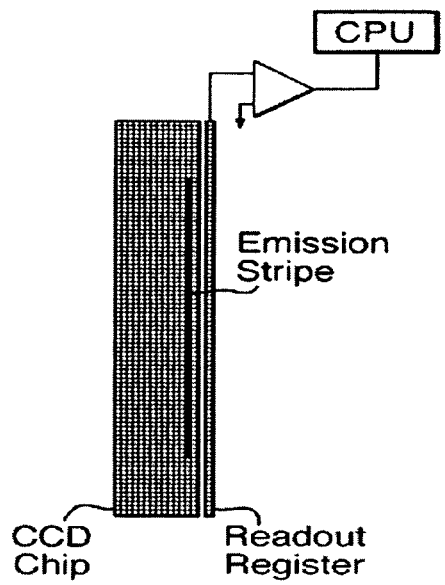
FIGS. 6A, 6B and 6C illustrate a rectangular CCD camera and readout register.
Figure 6B:
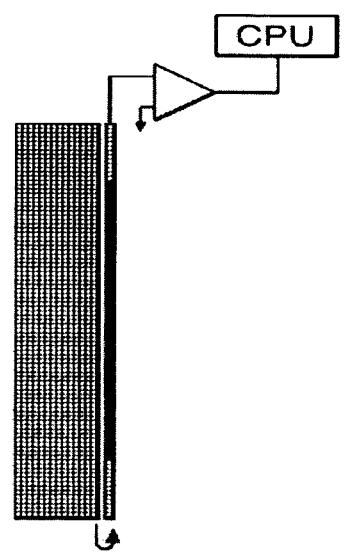
Figure 6C:
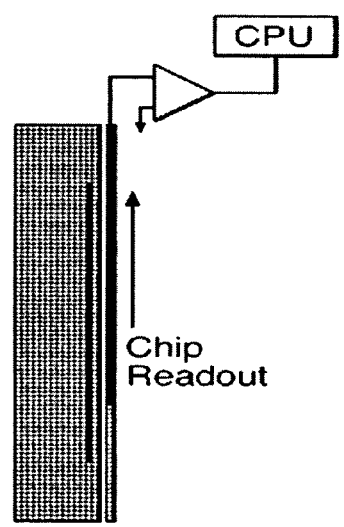

Presently, the highest detection efficiency, lowest noise detection devices having sufficient read-out speed for the present applications are CCD cameras. In FIGS. 6A, 6B and 6C, a rectangular CCD camera is depicted having an m×n array of detector elements where m is substantially less than n. The image of the fluorescence emission covers one row that is preferably proximate to the read register. This minimizes transfer time and avoids accumulating spurious counts into the signal from the rows between the illuminated row and the read-register.

In principle, one could set the magnification of the optical system so that the height of the image of the slit $SF_2$ on the CCD camera is one pixel, as depicted in FIGS. 4A, 4B and 4C. In practice, it is difficult to maintain perfect alignment between the illumination line and the camera row-axis, and even more difficult to maintain alignment among three cameras and the illumination in the multi-wavelength embodiment as exemplified in FIGS. 3 and 4. By binning together a few of the detector elements, exemplarily two to five, in each column of the camera the alignment condition can be relaxed while suffering a minimal penalty in read-noise or read-time.

An additional advantage of the preferred embodiment having one or more rectangular CCD cameras as detection devices in conjunction with a variable-width detection spatial filter, $SF_2$ in FIGS. 3 and 4 and 210 in FIG. 2, each disposed in a plane conjugate to the object plane, is elucidated by the following. As discussed above, in one embodiment of the present invention the detection spatial filter is omitted and a line-camera is used as a combined detection spatial filter and detection device. But as was also discussed above, a variable-width detection spatial filter permits the optimization of the detection volume so as to optimize the sample-dependent signal-to-noise ratio. The following preferred embodiment retains the advantage of a line-camera, namely speed, and the flexibility of a variable detection volume. The magnification is set so as to image a diffraction-limited line of height h onto one row of the camera. The width of the detection spatial filter d is preferably variable $h \leq d \leq 10h$. The detectors in the illuminated columns of the camera are binned, prior to reading, which is an operation that requires a negligible time compared to the exposure- and read-times.

In one preferred embodiment, the cameras are Princeton Instruments NTE/CCD-1340/100-EMD. The read-rate in a preferred embodiment is 1 MHz at a few electrons of read-noise. The pixel format is 1340×100, and the camera can be wired to shift the majority of the rows (80%) away from the region of interest, making the camera effectively 1340×20.

In addition to the above mentioned advantage of a continuous read camera, namely the absence of dead-time between successive acquisitions, an additional advantage is that it permits the acquisition of rectangular images having a length limited only by the extent of the sample. The length is determined by the lesser of the camera width and the extent of the line illumination. In a preferred embodiment the sample is disposed on the bottom of a well in a 96-well microtiter plate, the diameter of which is 7 mm. A strip 1 μm×1 mm is illuminated and the radiation emitted from the illuminated area is imaged onto the detection device. The optical train is designed such that the field-of-view is ~1 $mm^2$. According to the present invention, an image of the well-bottom can be generated at 1-μM pixelation over a 1×7-mm field.

Environmental Control

In an embodiment of the present invention, assays are performed on live cells. Live-cell assays frequently require a reasonable approximation to physiological conditions to run properly. Among the important parameters is temperature. It is desirable to incorporate a means to raise and lower the temperature, in particular, to maintain the temperature of the sample at 37C. In another embodiment, control over relative humidity, and/or $CO_2$ and/or $O_2$ is necessary to maintain the viability of live cells. In addition, controlling humidity to minimize evaporation is important for small sample volumes.

Three embodiments providing a microtiter plate at an elevated temperature, preferably 37 degrees C., compatible with the LCI system follow.

The imaging system preferably resides within a light-proof enclosure. In a first embodiment, the sample plate is maintained at the desired temperature by maintaining the entire interior of the enclosure at that temperature. At 37 degrees C., however, unless elevated humidity is purposefully maintained, evaporation cooling will reduce the sample volume limiting the assay duration.

A second embodiment provides a heated cover for the microwell plate which allows the plate to move under the stationary cover. The cover has a single opening above the well aligned with the optical axis of the microscope. This opening permits dispensing into the active well while maintaining heating and limited circulation to the remainder of the plate. A space between the heated cover plate and microwell plate of approximately 0.5 mm allows free movement of the microwell plate and minimizes evaporation. As the contents of the interrogated well are exposed to ambient conditions though the dispenser opening for at most a few seconds, said contents suffer no significant temperature change during the measurement.

In a third embodiment, a thin, heated sapphire window is used as a plate bottom enclosure. A pattern of resistive heaters along the well separators maintain the window temperature at the desired level.

In additional embodiments, the three disclosed methods can be variously combined.

In an additional preferred embodiment of the invention, employed in automated screening assays, the imaging system is integrated with plate-handling robots, such as the Zymark Twister.

Data Processing System

Figure 7:
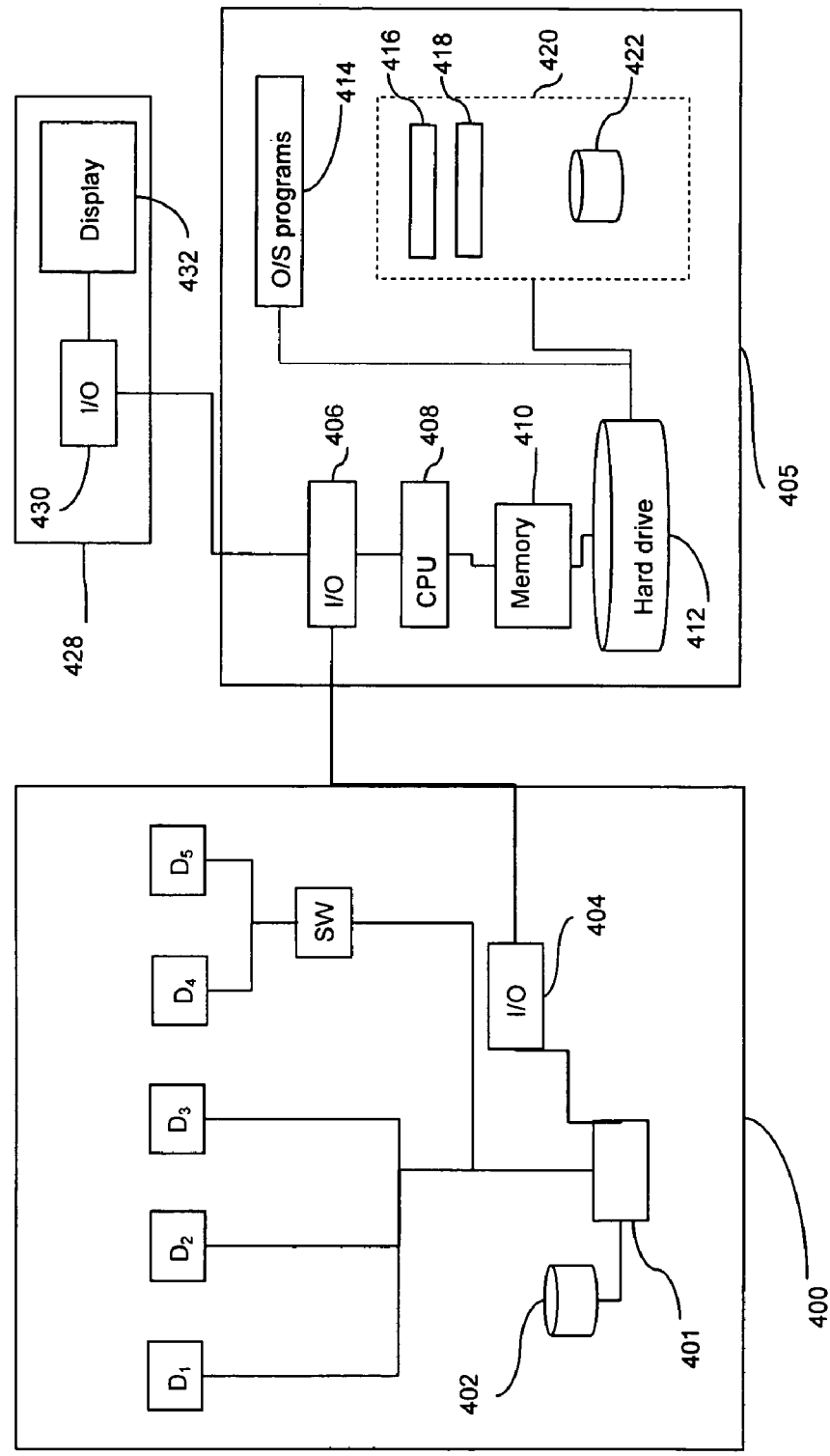
FIG. 7 is a schematic illustration showing data processing components in an imaging data processing system arranged in accordance with an embodiment of the invention.

FIG. 7 shows a schematic illustration of data processing components of a system arranged in accordance with the invention. The system, based on the Amersham Biosciences IN Cell Analyzer™ system, includes a confocal microscope 400 as described above, which includes the detectors $D_1$, $D_2$, $D_3$, $D_4$, $D_5$, the switch SW, a control unit 401, an image data store 402 and an Input/Output (I/O) device 404. An associated computer terminal 405 includes a central processing unit (CPU) 408, memory 410, a data storage device such as a hard disc drive 412 and I/O devices 406 which facilitate interconnection of the computer with the MDPU and the computer with a display element 432 of a screen 428 via a screen I/O device 430, respectively. Operating system programs 414 are stored on the hard disc drive 412, and control, in a known manner, low level operation of the computer terminal 405. Program files and data 420 are also stored on the hard disc drive 412, and control, in a known manner, outputs to an operator via associated devices and output data stored on the hard disc drive. The associated devices include a display 432 as an element of the screen 428, a pointing device (not shown) and keyboard (not shown), which receive input from, and output information to, the operator via further I/O devices (not shown). Included in the program files 420 stored on the hard drive 412 are an image processing and analysis application 416, an assay control application 418, and a database 422 for storing image data received from the microscope 400 and output files produced during data processing. The image processing and analysis application 418 may be a customized version of known image processing and analysis software packages.

The performance of an assay using the confocal microscope 400 is controlled using control application 418, and the image data are acquired. After the end of acquisition of image data for at least one well in a microtiter plate by at least one detector $D_1$, $D_2$, $D_3$, the image data are transmitted to the computer 405 and stored in the database 422 on the computer terminal hard drive 412, at which point the image data can be processed using the image processing and analysis application 416, as will be described in greater detail below.

Luminescent Reporters Expressed in Cells

Numerous variations of the assay methods described below can be practiced in accordance with the invention. In general, a characteristic spatial and/or temporal distribution of one or more luminescence reporters in cells is used to quantify the assay. Advantageously, luminescence is observed from an essentially planar surface using a line-scan confocal microscope as described above.

In preferred embodiments of the invention, luminescent reporters are provided in a manner as described in our previous International patent application WO 03/031612. The position in the cell cycle of a population of cells is determined by:

a) expressing in the cells a nucleic acid reporter construct, preferably a DNA construct, comprising a nucleic acid sequence encoding a detectable live-cell reporter molecule operably linked to and under the control of:

i) at least one cell cycle phase-specific expression control element, and ii) a destruction control element;

wherein said reporter construct is expressed in a cell at a predetermined point in the cell cycle; and b) determining the position of cells in the cell cycle by monitoring luminescent signals emitted by the reporter molecule.

The nucleic acid reporter construct is also preferably linked to and under the control of a cell cycle phase-specific spatial localisation control element.

The cell cycle phase-specific expression control element is typically a DNA sequence that controls transcription and/or translation of one or more nucleic acid sequences and permits the cell cycle specific control of expression. Any expression control element that is specifically active in one or more phases of the cell cycle may suitably be used for construction of the cycle position reporter construct.

Suitably, the cell cycle phase specific expression control element may be selected from cell cycle specific promoters and other elements that influence the control of transcription or translation in a cell cycle specific manner. Where the expression control element is a promoter, the choice of promoter will depend on the phase of the cell cycle selected for study.

Suitable promoters include: cyclin B1 promoter (Cogswell et al, Mol. Cell Biol., (1995), 15(5), 2782-90, Hwang et al, J. Biol. Chem., (1995), 270(47), 28419-24, Piaggio et al, Exp. Cell Res., (1995), 216(2), 396-402); Cdc25B promoter (Korner et al, J. Biol. Chem., (2001), 276(13), 9662-9); cyclin A2 promoter (Henglein et al, Proc. Nat. Acad. Sci. USA, (1994), 91(12), 5490-4, Zwicker et al, Embo J., (1995), 14(18), 4514-22); Cdc2 promoter (Tommasi and Pfeifer, Mol. Cell Biol., (1995), 15(12), 6901-13, Zwicker et al, Embo J (1995), 14(18), 4514-22), Cdc25C promoter (Korner and Muller, J. Biol. Chem., (2000), 275 (25), 18676-81, Korner et al, Nucl. Acids Res., (1997), 25(24), 4933-9); cyclin E promoter (Botz et al, Mol. Cell Biol., (1996), 16(7), 3401-9, Korner and Muller, J. Biol. Chem., (2000), 275(25), 18676-81); Cdc6 promoter (Hateboer et al, Mol. Cell Biol., (1998), 18(11), 6679-97, Yan et al, Proc. Nat. Acad. Sci. USA, (1998), 95(7),3603-8); DHFR promoter (Shimada et al, J. Biol. Chem., (1986), 261(3), 1445-52, Shimada and Nienhuis, J. Biol. Chem., (1985), 260(4), 2468-74) and histones promoters (van Wijnen et al, Proc. Nat. Acad. Sci. USA, (1994), 91, 12882-12886).

Suitably, the cell cycle phase specific expression control element may be selected from cell cycle specific IRES elements and other elements that influence the control of translation in a cell cycle specific manner. An IRES element is an internal ribosomal entry site that allows the binding of a ribosome and the initiation of translation to occur at a region of mRNA which is not the 5'-capped region. A cell cycle-specific IRES element restricts cap-independent initiation of translation to a specific stage of the cell cycle (Sachs, A. B., Cell, (2000), 101, 243-5). Where the expression control element is selected to be an IRES, suitably its selection will depend on the cell cycle phase under study. In this case, a constitutively expressed (e.g. CMV or SV40) or inducible (e.g. pTet-on pTet-off system, Clontech) promoter may be used to control the transcription of the bicistronic mRNA (Sachs, A. B., Cell, (2000), 101, 243-5). Alternatively, a non cell cycle phase-dependent IRES element (e.g. the EMCV IRES found in pIRES vectors, BD Clontech) may be used in conjunction with a cell cycle specific promoter element. Alternatively, more precise control of expression of the reporter may be obtained by using a cell cycle phase specific promoter in conjunction with a cell cycle phase specific IRES element.

IRES elements suitable for use in the invention include: G2-IRES (Cornelis et al, Mol. Cell, (2000), 5(4), 597-605); HCV IRES (Honda et al, Gastroenterology, (2000), 118, 152-162); ODC IRES (Pyronet et al, Mol. Cell, (2000), 5, 607-616); c-myc IRES (Pyronnet et al, Mol. Cell, (2000), 5(4), 607-16) and p58 PITSLRE IRES (Cornelis et al, Mol. Cell, (2000), 5(4), 597-605).

Table 1 lists some preferred expression control elements that may be used in accordance with the invention, and indicates the cell cycle phase in which each element is activated.

TABLE 1

Cell Cycle Phase-Specific Expression Control Elements

| Element | Timing |
|---|---|
| Cyclin B1 promoter | G2 |
| Cdc25B promoter | S/G2 |
| Cyclin A2 promoter | S |
| Cdc2 promoter | S |
| Cdc25C promoter | S |
| Cyclin E promoter | late G1 |
| Cdc6 promoter | late G1 |
| DHFR promoter | late G1 |
| Histones promoters | late G1/S |
| G2-IRES | G2 |
| HCV IRES | M |
| ODC IRES | G2/M |
| c-myc IRES | M |
| p58 PITSLRE IRES | G2/M |

The destruction control element is a DNA sequence encoding a protein motif that controls the destruction of proteins containing that sequence. Suitably, the destruction control element may be cell cycle mediated, for example: Cyclin B1 D-box (Glotzer et al, Nature, (1991), 349, 132-138, Yamano et al, EMBO J., (1998), 17(19), 5670-8, Clute and Pines, Nature Cell Biology, (1999), 1, 82-87); cyclin A N-terminus (den Elzen and Pines, J. Cell Biol., (2001), 153(1), 121-36, Geley et al, J. Cell Biol., (2001), 153, 137-48); KEN box (Pfleger and Kirschner, Genes Dev, (2000), 14(6), 655-65), Cyclin E (Yeh et al, Biochem Biophys Res Commun., (2001) 281, 884-90), Cln2 cyclin from *S. cerevisiae* (Berset et al, Mol. Cell Biol., (2002), pp 4463-4476) and p27Kip1 (Montagnoli et al, Genes Dev., (1999), 13(9), 1181-1189, Nakayama et al, EMBO J., (2000), 19(9), 2069-81, Tomoda et al, Nature, (1999), 398 (6723), 160-5).

Table 2 lists destruction control elements that may be used according to the invention 15 and indicates the cell cycle phase in which each element is activated.

TABLE 2

Destruction Control Elements

| Element | Timing |
|---|---|
| Cyclin B1 D-box | Metaphase through to G1 phase |
| Cyclin A N-terminus | Prometaphase through to G1 phase |
| KEN box | anaphase/G1 |
| p27Kip1 | G1 |
| Cyclin E | G1/S boundary |
| Cln2 | G1/S boundary |

Alternatively, the destruction control element may be non cell-cycle mediated, such as PEST sequences as described by Rogers et al, Science, (1986), 234, 364-8. Examples of non cell-cycle mediated destruction control elements include sequences derived from casein, ornithine decarboxylase and proteins that reduce protein half-life. Use of such non cell-cycle mediated destruction control sequences in the method of the invention provides means for determining the persistence time of the cell cycle reporter following induction of expression by a cell cycle specific promoter.

Suitably, the live-cell reporter molecule encoded by the nucleic acid sequence may be selected from the group consisting of fluorescent proteins and enzymes. Preferred fluorescent proteins include Green Fluorescent Protein (GFP) from *Aequorea victoria* and derivatives of GFP such as functional GFP analogues in which the amino acid sequence of wild type GFP has been altered by amino acid deletion, addition, or substitution. Suitable GFP analogues for use in the present invention include EGFP (Cormack, B. P. et al, Gene, (1996), 173, 33-38); EYFP and ECFP (U.S. Pat. No. 6,066,476, Tsien, R. et al); F64L-GFP (U.S. Pat. No. 6,172,188, Thastrup, O. et al); BFP, (U.S. Pat. No. 6,077,707, Tsien, R. et al). Other fluorescent proteins include DsRed, HcRed and other novel fluorescent proteins (BD Clontech and Labas, Y. A. et al, Proc Natl Acad Sci USA (2002), 99, 4256-61) and Renilla GFP (Stratagene). Suitable enzyme reporters are those which are capable of generating a detectable (e.g. a fluorescent or a luminescent) signal in a substrate for that enzyme. Particularly suitable enzyme/substrates include: nitroreductase/Cy-Q (as disclosed in WO 01/57237) and β-lactamase/CCF4.

In a preferred embodiment, the nucleic acid reporter construct may optionally include a cell cycle phase-specific spatial localisation control element comprising a DNA sequence encoding a protein motif that is capable of controlling the sub-cellular localisation of the protein in a cell cycle specific manner. Such a localisation control element may be used advantageously according to the invention where:

i) a specific sub-cellular localisation of the reporter is desirable; and/or ii) more precise determination of the cell cycle position is required.

It may be required to determine the sub-cellular localisation of the reporter either to ensure its effective operation and/or destruction. More precise determination of the cell cycle position may be possible using a localisation control element since this will permit measurement of both intensity and location of the reporter signal.

Suitable spatial localisation control elements include those that regulate localisation of a cell cycle control protein, for example the cyclin B1 CRS.

Figure 8A:
FIG. 8 is a schematic diagram illustrating cell cycle position nucleic acid reporter constructs used in an embodiment of the present invention.
Figure 8B:
Figure 8C:

The term "operably linked" as used herein indicates that the elements are arranged so that they function in concert for their intended purposes, e.g. transcription initiates in a promoter and proceeds through the DNA sequence coding for the fluorescent protein of the invention. FIGS. 8A, 8B and 8C illustrate the general construction of a DNA construct according to the invention, in which FIG. 8A shows a construct utilising a cell cycle phase-specific promoter and no internal ribosome entry site (IRES) element, FIG. 8B shows a construct utilising an IRES element to facilitate mammalian selection, and FIG. 8C shows a construct utilising a constitutive or inducible mammalian promoter and a cell cycle phase-specific IRES as the expression control element. In each case A represents a cell cycle phase-specific expression control (promoter), B represents a cell cycle phase specific destruction control element, C represents a cell cycle phase specific localisation control element, D represents a reporter gene, E represents a non-cell cycle specific IRES element, F represents a mammalian selectable marker, G represents a mammalian constitutive promoter and H represents a cell cycle specific IRES element In a preferred embodiment of the invention, the construct comprises a cyclin B1 promoter, a cyclin B1 destruction box (D-box), a cyclin B1 cytoplasmic retention sequence (CRS) and a green fluorescent protein (GFP).

In one embodiment, the nucleic acid reporter construct comprises an expression vector comprising the following elements:

a) a vector backbone comprising:

i) a bacterial origin of replication; and ii) a bacterial drug resistance gene;

b) a cell cycle phase specific expression control element;
c) a destruction control element; and
d) a nucleic acid sequence encoding a reporter molecule.

Optionally, the nucleic acid reporter construct additionally contains a cell cycle phase-specific spatial localisation control element and/or a eukaryotic drug resistance gene, preferably a mammalian drug resistance gene.

Expression vectors may also contain other nucleic acid sequences, such as polyadenylation signals, splice donor/splice acceptor signals, intervening sequences, transcriptional enhancer sequences, translational enhancer sequences and the like. Optionally, the drug resistance gene and the reporter gene may be operably linked by an internal ribosome entry site (IRES), which is either cell cycle specific (Sachs, et al, Cell, (2000), 101, 243-245) or cell cycle independent (Jang et al, J. Virology, (1988), 62, 2636-2643 and Pelletier and Sonenberg, Nature, (1988), 334, 320-325), rather than the two genes being driven from separate promoters. When using a non cell-cycle specific IRES element the pIRES-neo and pIRES-puro vectors commercially available from Clontech may be used.

Figure 9:
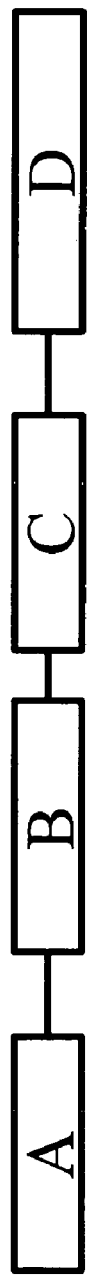
FIG. 9 shows a DNA construct for determining the G2/M phase of the cell cycle.

In a particular embodiment, the nucleic acid reporter construct is assembled from a DNA sequence encoding the cyclin B1 promoter operably linked to DNA sequences encoding 171 amino acids of the amino terminus of cyclin B1 and a DNA sequence encoding a green fluorescent protein (GFP) (FIG. 9). The construct illustrated in FIG. 9 contains a cyclin B1 promoter (A), cyclin B1 destruction box (D-box) (B), cyclin B1 CRS (C) and a GFP reporter (D). Motifs controlling the localisation and destruction of cyclin B1 have all been mapped to ~150 amino acids in the amino terminus of the molecule. Consequently, an artificial cell cycle marker can be constructed using only sequences from the amino terminus of cyclin B1, which will not interfere with cell cycle progression since it lacks a specific sequence, termed the cyclin box, (Nugent et al, J. Cell. Sci., (1991), 99, 669-674) which is required to bind to and activate a partner kinase. Key regulatory motifs required from the amino terminus sequence of cyclin B1 are:

i) a nine amino acid motif termed the destruction box (D-box). This is necessary to target cyclin B1 to the ubiquitination machinery and, in conjunction with at least one C-terminal lysine residue, this is also required for its cell-cycle specific degradation;
  ii) an approximately ten amino acid nuclear export signal (NES). This motif is recognized, either directly or indirectly, by exporting 1 and is sufficient to maintain the bulk of cyclin B1 in the cytoplasm throughout interphase;
    iii) approximately four mitosis-specific phosphorylation sites that are located in and adjacent to the NES and confer rapid nuclear import and a reduced nuclear export at mitosis.

Figure 10:
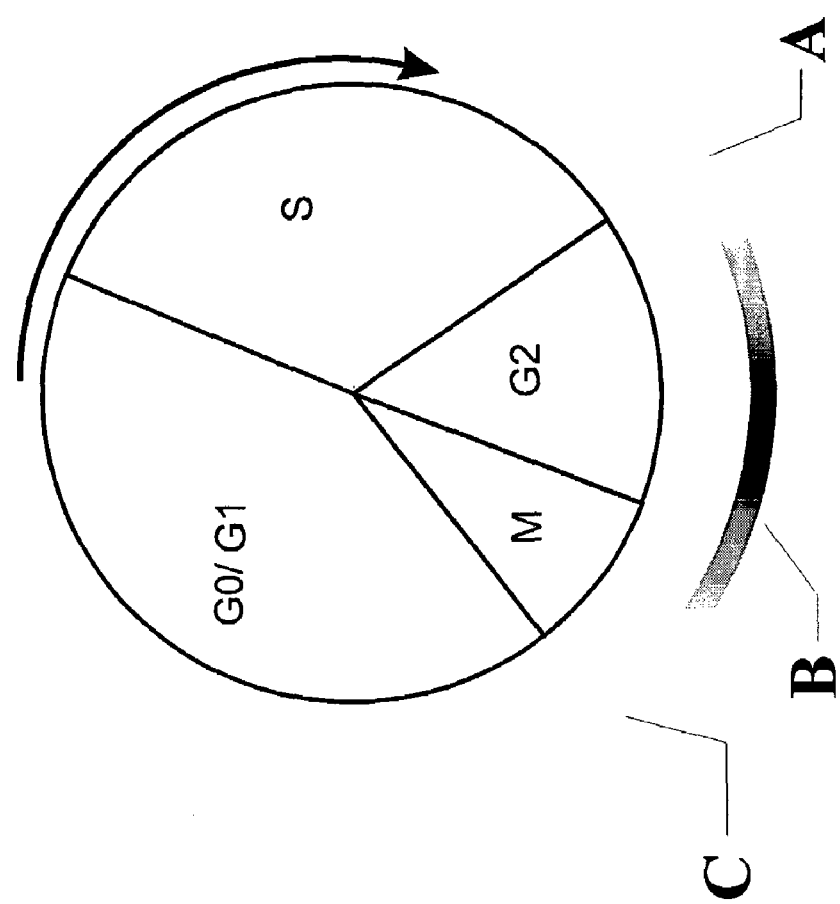
FIG. 10 is a schematic diagram illustrating cyclin B1 regulation during cell cycle progression. The cell cycle proceeds in the direction of the arrow with cyclin B1 expression driven by a cell cycle phase-specific promoter which initiates expression at the end of the S phase and peaks during G2 (A). At the start of mitosis (B) cyclin B1 translocates from the cytoplasm to the nucleus and from metaphase onwards (C) the protein is specifically degraded.

When expressed in a eukaryotic cell, the construct will exhibit cell cycle specific expression and destruction of the GFP reporter which parallels the expression and degradation of endogenous cyclin B1. Hence, measurement of GFP fluorescence intensity permits identification of cells in the G2/M phase of the cell cycle (FIG. 10). Furthermore, since the fluorescent product of the construct will mimic the spatial localisation of endogenous cyclin B1, analysis of the sub-cellular distribution of fluorescence permits further precision in assigning cell cycle position. At prophase, cyclin B1 rapidly translocates into the nucleus, consequently the precise localisation of GFP fluorescence in the cell can be used to discriminate cells transitioning from interphase to mitosis. Once a cell reaches metaphase, and the spindle assembly checkpoint is satisfied, cyclin B1 is very rapidly degraded, and consequently the disappearance of GFP fluorescence can be used to identify cells at mid-M phase.

Expression of the construct in a population of unsynchronised cells will result in each cell exhibiting cyclical expression and destruction of the fluorescent product from the construct, resulting in a continuous blinking pattern of fluorescence from all cells in the population. Analysis of the fluorescence intensity of each cell with time consequently yields dynamic information on the cell cycle status of each cell.

Further embodiments of the nucleic acid reporter construct according to the first aspect may be constructed by selecting suitable alternative cell cycle control elements, for example from those shown in Tables 1 and 2, to design cell cycle phase reporters which report a desired section of the cell cycle.

The construction and use of expression vectors and plasmids are well known to those of skill in the art. Virtually any mammalian cell expression vector may be used in connection with the cell cycle markers disclosed herein. Examples of suitable vector backbones which include bacterial and mammalian drug resistance genes and a bacterial origin of replication include, but are not limited to: pCI-neo (Promega), pcDNA (Invitrogen) and pTriEx1 (Novagen). Suitable bacterial drug resistance genes include genes encoding for proteins that confer resistance to antibiotics including, but not restricted to: ampicillin, kanamycin, tetracyclin and chloramphenicol. Eurkaryotic drug selection markers include agents such as: neomycin, hygromycin, puromycin, zeocin, mycophenolic acid, histidinol, gentamycin and methotrexate.

The DNA construct may be prepared by the standard recombinant molecular biology techniques of restriction digestion, ligation, transformation and plasmid purification by methods familiar to those skilled in the art and are as described in Sambrook, J. et al (1989), Molecular Cloning—A Laboratory Manual, Cold Spring Harbor Laboratory Press. Alternatively, the construct can be prepared synthetically by established methods, e.g. the phosphoramidite method described by Beaucage and Caruthers, (Tetrahedron Letters, (1981), 22, 1859-1869) or the method described by Matthes et al (EMBO J., (1984), 3, 801-805). According to the phosphoramidite method, oligonucleotides are synthesised, e.g. in an automatic DNA synthesizer, purified, annealed, ligated and cloned into suitable vectors. The DNA construct may also be prepared by polymerase chain reaction (PCR) using specific primers, for instance, as described in U.S. Pat. No. 4,683,202 or by Saiki et al (Science, (1988), 239, 487-491). A review of PCR methods may be found in PCR protocols, (1990), Academic Press, San Diego, Calif., U.S.A.

During the preparation of the DNA construct, the gene sequence encoding the reporter must be joined in frame with the cell cycle phase specific destruction control element and optionally the spatial localisation control element. The resultant DNA construct should then be placed under the control of one or more suitable cell cycle phase specific expression control elements.

The host cell into which the construct or the expression vector containing such a construct is introduced, may be any cell which is capable of expressing the construct and may be selected from eukaryotic cells for example, from the group consisting of a mammalian cell, a fungal cell, a nematode cell, a fish cell, an amphibian cell, a plant cell and an insect cell.

The prepared DNA reporter construct may be transfected into a host cell using techniques well known to the skilled person. One approach is to temporarily permeabilise the cells using either chemical or physical procedures. These techniques may include: electroporation (Tur-Kaspa et al, Mol. Cell Biol. (1986), 6, 716-718; Potter et al, Proc. Nat. Acad. Sci. USA, (1984), 81, 7161-7165), a calcium phosphate based method (eg. Graham and Van der Eb, Virology, (1973), 52, 456-467 and Rippe et al, Mol. Cell Biol., (1990), 10, 689-695) or direct microinjection.

Alternatively, cationic lipid based methods (eg. the use of Superfect (Qiagen) or Fugene6 (Roche) may be used to introduce DNA into cells (Stewart et al, Human Gene Therapy, (1992), 3, 267; Torchilin et al, FASEB J, (1992), 6, 2716; Zhu et al, Science, (1993), 261, 209-211; Ledley et al, J. Pediatrics, (1987), 110, 1; Nicolau et al, Proc. Nat. Acad. Sci., USA, (1983), 80,1068; Nicolau and Sene, Biochem. Biophys. Acta, (1982), 721, 185-190). Jiao et al, Biotechnology, (1993), 11, 497-502) describe the use of bombardment mediated gene transfer protocols for transferring and expressing genes in brain tissues which may also be used to transfer the DNA into host cells.

A further alternative method for transfecting the DNA construct into cells, utilises the natural ability of viruses to enter cells. Such methods include vectors and transfection protocols based on, for example, Herpes simplex virus (U.S. Pat. No. 5,288,641), cytomegalovirus (Miller, Curr. Top. Microbiol. Immunol., (1992), 158, 1), vaccinia virus (Baichwal and Sugden, 1986, in Gene Transfer, ed. R. Kucherlapati, New York, Plenum Press, p 117-148), and adenovirus and adeno-associated virus (Muzyczka, Curr. Top. Microbiol. Immunol., (1992), 158, 97-129).

Examples of suitable recombinant host cells include HeLa cells, Vero cells, Chinese Hamster ovary (CHO), U2OS, COS, BHK, HepG2, NIH 3T3 MDCK, RIN, HEK293 and other mammalian cell lines that are grown in vitro. Such cell lines are available from the American Tissue Culture Collection (ATCC), Bethesda, Md., U.S.A. Cells from primary cell lines that have been established after removing cells from a mammal followed by culturing the cells for a limited period of time are also intended to be included in the present invention.

Cell lines which exhibit stable expression of a cell cycle position reporter may also be used in establishing xenografts of engineered cells in host animals using standard methods. (Krasagakis, K. J et al, Cell Physiol., (2001), 187(3), 386-91; Paris, S. et al, Clin. Exp. Metastasis, (1999), 17(10), 817-22). Xenografts of tumour cell lines engineered to express cell cycle position reporters will enable establishment of model systems to study tumour cell division, stasis and metastasis and to screen new anticancer drugs.

Use of engineered cell lines or transgenic tissues expressing a cell cycle position reporter as allografts in a host animal will permit study of mechanisms affecting tolerance or rejection of tissue transplants (Pye D and Watt, D. J., J. Anat., (2001), 198 (Pt 2), 163-73; Brod, S. A. et al, Transplantation (2000), 69(10), 2162-6).

To perform the method for determining the cell cycle position of a cell according to the second aspect, cells transfected with the DNA reporter construct may be cultured under conditions and for a period of time sufficient to allow expression of the reporter molecule at a specific stage of the cell cycle. Typically, expression of the reporter molecule will occur between 16 and 72 hours post transfection, but may vary depending on the culture conditions. If the reporter molecule is based on a green fluorescent protein sequence the reporter may take a defined time to fold into a conformation that is fluorescent. This time is dependent upon the primary sequence of the green fluorescent protein derivative being used. The fluorescent reporter protein may also change colour with time (see for example, Terskikh, Science, (2000), 290, 1585-8) in which case imaging is required at specified time intervals following transfection.

In the embodiment of the invention wherein the nucleic acid reporter construct comprises a drug resistance gene, following transfection and expression of the drug resistance gene (usually 1-2 days), cells expressing the modified reporter gene may be selected by growing the cells in the presence of an antibiotic for which transfected cells are resistant due, to the presence of a selectable marker gene. The purpose of adding the antibiotic is to select for cells that express the reporter gene and that have, in some cases, integrated the reporter gene, with its associated promoter, IRES elements, enhancer and termination sequences into the genome of the cell line. Following selection, a clonal cell line expressing the construct can be isolated using standard techniques. The clonal cell line may then be grown under standard conditions and will express reporter molecule and produce a detectable signal at a specific point in the cell cycle.

EXAMPLES OF PRODUCTION OF STABLE CELL LINES

Example 1

Preparation of DNA Construct i) The N-terminal third of the cyclin B1 mRNA (amino acids 1-171), encoding the cyclin B1 destruction box and the NES was amplified with HindIII and BamHI ends using standard PCR techniques and the following primers:

```
                                              (SEQ ID NO: 1)
   5'- GGGAAGCTTAGGATGGCGCTCCGAGTCACCAGGAAC -3'

(SEQ ID NO: 2)
   5'- GCCGGATCCCACATATTCACTACAAAGGTT -3'.
``` ii) The gene for wtGFP was amplified with primers designed to introduce restriction sites that would facilitate construction of fusion proteins. The PCR product was cloned into pTARGET (Promega) according to manufacturer's instructions and mutations (F64L/S175G/E222G) were introduced using the QuikChange site-directed mutagenesis kit (Stratagene). Constructs were verified by automated DNA sequencing. DNA encoding the mutant GFP was then cloned downstream of the cyclin B1 N-terminal region using BamHI and SalI restriction sites.

iii) The cell cycle dependent region of the cyclin B1 promoter (−150→+182) was amplified with SacII and HindIII sites and cloned upstream of the Cyclin B1 N-terminal region and the GFP fusion protein.

iv) The promoter and recombinant protein encoding DNA was excised and cloned in place of the CMV promoter in a BglII/NheI cut pCI-Neo derived vector.

Example 2

Effect of Cell Cycle Blocking Agents on GFP Fluorescence From Cell Cycle Phase Marker Using Transiently Transfected Cells U2OS cells (ATCC HTB-96) were cultured in wells of a 96 well microtitre plate. Cells were transfected with a cell cycle reporter construct prepared according to Example 1, comprising a cyclin B1 promoter operably linked to sequences encoding the cyclin B1 D-box, the cyclin B1 CRS, and GFP in a pCORON4004 vector (Amersham Biosciences) using Fugene 6 (Roche) as the transfection agent.

Following 24 hours of culture, cells were exposed to the specific cell cycle blockers mimosine (blocks at G1/S phase boundary) or demecolcine (blocks in M phase). Control cells were exposed to culture media alone.

Cells were incubated for a further 24 hours and then analysed for nuclear GFP expression using a confocal scanning imager with automated image analysis (IN Cell Analysis System, Amersham Biosciences).

Cells exposed to demecolcine showed increased fluorescence compared to control cells while cells exposed to mimosine showed decreased fluorescence compared to control cells. Cells blocked in G1/S phase (mimosine treated), prior to the time of activation of the cyclin B1 promoter, show reduced fluorescence, while cells blocked in M phase (demecolcine treated), prior to the time of action of the cyclin B1 D-box, show increased fluorescence.

Example 3

Microinjection of the Construct

HeLa cells were micro-injected with the construct prepared according to Example 1 and examined by time lapse microscopy. Differential interference contrast (DIC) images were made along with the corresponding fluorescence images. A cell in metaphase showed bright fluorescence in the nucleus. The same cell was imaged similarly at later times in anaphase and late anaphase. The DIC images showed the division of the cell into two daughter cells, the corresponding fluorescence images showed the loss of fluorescence accompanying destruction of the fluorescent construct as the cell cycle progresses.

Example 4

Stable Cell Line Production

U2-OS cells (ATCC HTB-96) were transfected with the construct described in Example 1 and grown for several months in culture media containing 1 mg/ml geneticin to select for cells stably expressing the construct. A number of clones were picked by standard methods (e.g. described in Freshney, Chapter 11 in Culture of Animal Cells, (1994) Wiley-Liss Inc) and a clone containing fluorescent cells was isolated. This cell line was maintained at 37° C. in culture media containing 25 mM HEPES.

Example 5

Preparation of a Brighter Stable Cell Line

The green fluorescent protein reporter sequence in the vector described in example 1 was replaced with enhanced GFP (EGFP; Cormack, B. P. et al, Gene, (1996), 173, 33-38; BD Clontech) by standard methods. The EGFP gene is a brighter form of GFP containing the mutations F64L and S65T. In addition, EGFP contains codons that have been altered to optimise expression in mammalian cells. This new construct was transfected into U2-OS cells and a number of colonies were isolated by selection with geneticin followed by sorting of single cells using a fluorescence activated cell sorter. These clones showed brighter fluorescence than those generated in example 4 and as expected fluorescence intensity and location appeared to vary according to the cell cycle phase of the cell.

Assays and Image Acquisition

According to embodiments of the invention, screening assays are conducted using libraries of chemical compounds. One or more multiwell plates are prepared using a cell line as described above. Whilst in the following embodiments a cell line including a cell cycle reporter construct as described in Example 1 above is used, it should be appreciated that any other of the described embodiments of cell line, or indeed other organisms, can be used in alternative embodiments. A controlled amount of cells, referred to herein as a population is placed in a carrier solution in each of the wells of the plate and allowed to establish for a predetermined period, for example 24 hours. Next, a different one of the library of chemical compounds is added in a controlled concentration and amount to each of the wells and allowed to stand for a predetermined period, for example 24 hours. In some embodiments of the invention, a nuclear stain is added before imaging is conducted. In other embodiments of the invention, no nuclear stain is added before imaging is conducted. Next, imaging is conducted for each well of the plate in turn, using a confocal microscope as described above. A small area in the centre of each well, at the bottom of the well, is imaged to acquire image data in one or more channels of the selected area. The fluorescence detected in the confocal microscope is converted into one or more digital images in which the digital values are proportional to the intensity of the fluorescent radiation incident on each pixel of the detection device.

Image Processing and Analysis

In general the processing and analysis of the image data in accordance with the invention comprises a number of discrete steps. The image data are analyzed to identify areas of the image corresponding to individual cells, as in step 1 of FIG. 1. Such object areas may be sub-cellular components of individual cells, such as the cell nuclei. A binary mask is generated from one of the digital images in which all values meeting one or more criteria are replaced by a "one", all values failing to meet the criteria are replaced by a "zero". Generally, the one or more criteria may include a threshold value determined from an image taken in a set-up procedure for the assay. The mask is searched for groups of contiguous value-one pixels to identify the object areas corresponding to individual cells. Next, measurements are made on the individual cells using the identified object areas.

Figure 11:
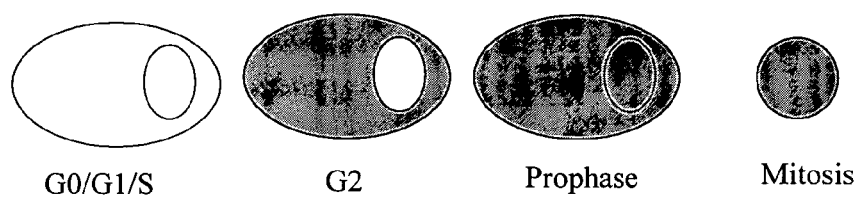
FIG. 11 is a schematic illustration showing typical intensity and distribution of signals in a cell including a fluorescent reporter in accordance with an embodiment of the invention, in each of the G0/G1S, G2, prophase and mitosis (M) cell cycle phases.

The cell cycle phase marker used has a fluorescence signal that varies according to the phase of the cell cycle of the cell in a manner which is illustrated in FIG. 11. Four different patterns can be distinguished in this embodiment of the invention:

1. G0/G1/S phase cells have relatively low expression of the cell cycle phase marker, both in the nucleus and the cytoplasm;
2. G2 cells have relatively low nuclear, and relatively high cytoplasmic, expression of the cell cycle phase marker
3. M cells have relatively high expression throughout the cell body;
4. P cells have relatively high nuclear, and relatively high cytoplasmic, expression of the cell cycle phase marker.

Figure 12:
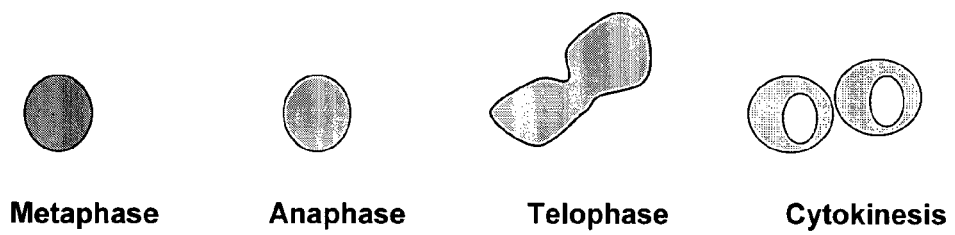
FIG. 12 is a schematic illustration showing typical intensity and distribution of signals in a cell including a fluorescent reporter in accordance with an embodiment of the invention, in each of the metaphase, anaphase, telophase, and cytokinesis cell cycle phases.

Furthermore, in an embodiment the mitotic cells can be distinguished into MP (metaphase) cells. A (anaphase) cells, T (telophase) cells and C (cytokinesis) cells. Schematic illustrations of the signal intensities and distributions of the fluorescent reporter in these cell cycle phases are shown in FIG. 12. Early G1 phase cells can also be distinguished in this embodiment.

A nuclear marker, producing fluorescence at a wavelength different to that of the cell cycle phase marker, is used in another embodiment to identify nuclear areas for each cell under analysis in the image data. The nuclear marker may be one of the toxic intercalating nuclear dyes (such as DRAQ5™ or a Hoechst™ dye, for example Hoechst 33342). Alternatively, in assays in which the same cell population is imaged and analysed to determine its relative cell cycle sub-populations a number of times during a time course study, a non-toxic nuclear marked may be used. Such a non-toxic marker may be in the form of an NLS-fluorescent protein fusion. For example, the Clontech™ pHcRed1-Nuc vector, when transfected into a cell line in accordance with the present invention, produces a red fluorescence signal in the nucleus. During image acquisition, an image of the cell nuclei is acquired in a first channel corresponding to the nuclear marker, a cell cycle phase analysis image is acquired in a second channel corresponding to the cell phase marker, and the two images are coregistered such that the pixels of each image are aligned.

The cell nuclei image is analysed first to identify nuclear areas in the image data. A nuclear signal threshold may be set to accurately differentiate the edges of the nuclear areas. A segmentation algorithm, for example a watershed segmentation algorithm (S. Beucher, F. Meyer, "Morphological Segmentation", Journal of Visual Communication and Image Representation, 1:21-46, 1990 and Vincent, Soille, IEEE Transactions on Pattern Analysis and Machine Intelligence, 13:583-598, 1991) is applied to the thresholded image to uniquely identify the area of the nucleus of each individual cell being analysed.

From each nuclear object area identified, two binary masks, defining object areas in which the cell measurements are to be taken, are generated—an eroded nuclear mask (to sample the cell cycle phase marker intensity signal in the central part of nucleus) and a thin cytoplasmic ring (to sample the cell cycle phase marker intensity signal in the cytoplasm near the nucleus). The nuclear object area is eroded from the edge of the nuclear object by a predetermined number of pixels, for example three pixels, to generate the eroded nuclear mask. To generate the thin cytoplasmic ring, representing the cytoplasmic area adjacent to the nucleus, the nuclear object is dilated from its edge by a predetermined number of pixels, for example two pixels.

Measurements on Individual Cells

The two masks, generated for each individual cell as described above, are then applied to the cell cycle phase analysis image.

Measurements are then derived from the image data, as in step 2 of FIG. 1. The fluorescence signal intensities in each pixel in the eroded nuclear mask area are averaged to produce a measurement of the average nuclear signal intensity ($I_n$) parameter which represents the average intensity over the nuclear area.

The fluorescence signal intensities in each pixel in the thin cytoplasmic ring are averaged to produce measurement of the average cytoplasmic signal intensity ($I_c$) parameter representing the average intensity within cytoplasmic sampling ring.

The ratio of the two measured average intensities is then taken to generate the nuclear/cytoplasmic ratio $$\left(\frac{I_n}{I_c}\right)$$

parameter, representing the ratio of nuclear and cytoplasmic average intensities.

A parameter set is associated with each cell identified from one or more object areas in the image data. The parameter set is derived from the measurements taken from the image data, at step 3 of FIG. 1. In the present example, the parameter set includes a floating point number representative of the nuclear/cytoplasmic ratio. However, the parameter set may consist of any number of measurements derived from the image. For example, if the cells were expressing several markers, the intensity of each marker would be a measurement for inclusion in the parameter set. The parameter set is derived automatically for each cell which is identified from an object area and the appropriate measurement values are put in the parameter set. The parameter set is saved to a database of classifying data when the associated cell is classified.

Measurements may be taken from any identified object area. For example, if the nucleus and cytoplasm are identified as object areas, one or more measurements could be taken from both, or either.

Measurements may be derived from a variety of parameters, including:

I, a parameter relating to an average image signal intensity within an identified object area;

F, a parameter relating to a fraction of pixels that deviate more than a given amount from an average signal intensity within an identified object area;

H, a parameter relating to the number of pixels with a signal intensity below a given threshold within an identified object area;

A, a parameter relating to a ratio between major and minor axes of an elliptical outline corresponding to an identified object area;

R, a parameter relating to a maximum width of an identified object area;

L, a parameter relating to an average width of an identified object area;

C, a parameter relating to signal texture within an identified object area;

M, a parameter relating to margination in an identified object area.

In a specific embodiment, one or more of the following parameters may be taken for each cell being analysed:

$A_{nuc}$, the area of the cell nucleus;

$A_{nuc}/A_{cell}$, the ratio of the area of the nucleus to the size of the cell;

$(W/L)_{nuc}$, the nuclear elongation (ratio of the lengths of the nucleus in the major and minor axes);

$P_{nuc}^2/4\pi A_{nuc}$, the form factor of the nucleus, which is equal to 1 for a perfectly round nucleus;

$P_{nuc}^2/4\pi A_{cell}$, the form factor of the cell, which is equal to 1 for a perfectly round nucleus;

$D/R_{g\ nuc}$, the nuclear displacement. D is the distance between the nucleus' and the cell's centres of gravity, and $R_{g\ nuc}$ is the gyration radius of the nucleus. Gyration radius of an object composed of N pixels is defined by:

$$R_g^2 = \frac{1}{N}\sum_{i=1}^{N}(r_i - r_{CG})2$$

$$r_{CG} = \frac{1}{N}\sum_{i=1}^{N}r_i,$$

where $r_i$ denotes the coordinates of the i-the pixel in the object, and $r_{CG}$ denotes the coordinates of the centre of gravity;

$LIR_{N/C}$, the local intensity ratio, which is the ratio of the average intensity of the nucleus to the surrounding cytoplasm;

$LIR_{C/Bckg}$, the ratio of cell intensity to the intensity of the background sampled in the immediate vicinity of the cell. The background vicinity may be determined by dilating a binarized image of the cell and its immediate vicinity, and then excluding the cell according to its original size from the binarized image;

$CV_{nuc}$, the ratio of the standard deviation/mean of the nuclear intensity;

$CV_{cyt}$, the ratio of the standard deviation/mean of the cytoplasmic intensity;

PDD, the peripheral density descriptor, which quantifies intensity concentration near an object's boundary. The object may be the nucleus, or the whole cell. PDD is defined by:

$$PDD = \frac{\sum_{i \subset O} U(r_i)|r_i|^2}{\langle U \rangle_O \Sigma_{i \subset O}|r_i|^2} = \frac{\sum_{i \subset O} U(r_i)|r_i|^2}{\langle U \rangle_O \cdot N \cdot R_g^2}$$

$U(r_i)$ is the intensity of the i-th pixel of the object O. $\langle U \rangle_O$ and $R_g$ are the object's average intensity and gyration radius, respectively. Calculation of the PDD as described in the above equation involves the determination of centre of the object, by the object's centre of gravity. An alternative PDD, $PDD_2$, may be calculated according to:

$$PDD2 = \frac{\sum_i U(r_i^{border})|r_i^{border}|^\alpha}{\langle U \rangle_O \sum_{i \subset O}|r_i^{border}|^\alpha}, \text{ where } \alpha < -1$$

$PDD_2$ is calculated based on border distance, not central distance: $r^{border}_i$ is the distance of a pixel from the object border, and $\alpha$ is an exponent controlling the sensitivity of the descriptor.

The above parameters are directly related to cell phenotypes. For example, the form factor of the nucleus will vary during cell division; therefore, the form factor of the nucleus may be one of the parameters used when a method according to the present invention is used to analyse a cell population on the basis of cell cycle. The parameters listed above are also robust with respect to artefacts caused by lighting changes.

Parameters may also be derived from the properties of organelles in the cytoplasm. Other parameters which may be used include the presence, absence or concentration of cellular features such as neurites, membrane ruffles, cytoplasmic granules, blebs, vesicles, vesicle clusters, cytoskeletal components, etc.

If one or more organelles (e.g. mitochondria, endosomes, endoplasmic reticula), or proteins present in vesicle-like or punctae distributions in the cytoplasm or in the nucleus, are identified within a cell, one or more of the following parameters may be taken:

I, average intensity;

LIR, average local intensity ratio—the ratio of the average intensity of the organelle to the average intensity of the background;

IOD, inter-organelle distance, and average of which is taken in the case where more than two organelles are segmented;

A, the average area of the organelle(s);

F, the form factor of the organelle, which may be determined as described above for the nucleus;

S, organelle size;

N, the number of organelles segmented.

Furthermore, the properties of chromosomes within the nucleus (e.g. chromosome condensation) may also be used a source of parameters for analysis by a method according to the present invention.

Segmentation may be applied to an image of a cell population in order to identify organelles of a characteristic size.

Two or more images may be taken from one sample and the images compared.

If a plurality of measurements is taken for a plurality of parameters, one or more of the measurements may be weighted in statistical importance. The measurement of a parameter that is known to be more reliably indicative of cell cycle phase would be weighted, as opposed to a parameter which is not as reliably indicative.

In embodiments where n measurements are taken from the cell image data, the parameter set may be represented as an n-dimensional vector in a space. Thus this parameter set is a feature vector, in a feature space. The representation of the parameter set as a feature vector in a feature space is described in more detail below.

Each cell identified as an object area from the image data is identified as being a member of a subpopulation, initially by a user, as in step 4 of FIG. 1. In an embodiment, the user may make an identification by selecting a cell by right-clicking a mouse when pointing at the cell on a screen, and then enter the identifying data, for example by left-clicking the mouse when pointing at a selected classification presented in a selection box. In the case of cell cycle phase classification, the identifying data will be one of the following: G0, G1, S, G2 and Mitotic (M), and may also include the phases of mitosis, prophase, metaphase, anaphase, and telophase.

The identifying data is received (step 5 in FIG. 1) and then saved to a database (step 6 of FIG. 1) in association with the selected cell's parameter set, to form classifying data. In this way, a database of classifying data, made up of parameter sets associated with identifying data, is built up for later use in automated classification.

Figure 13:
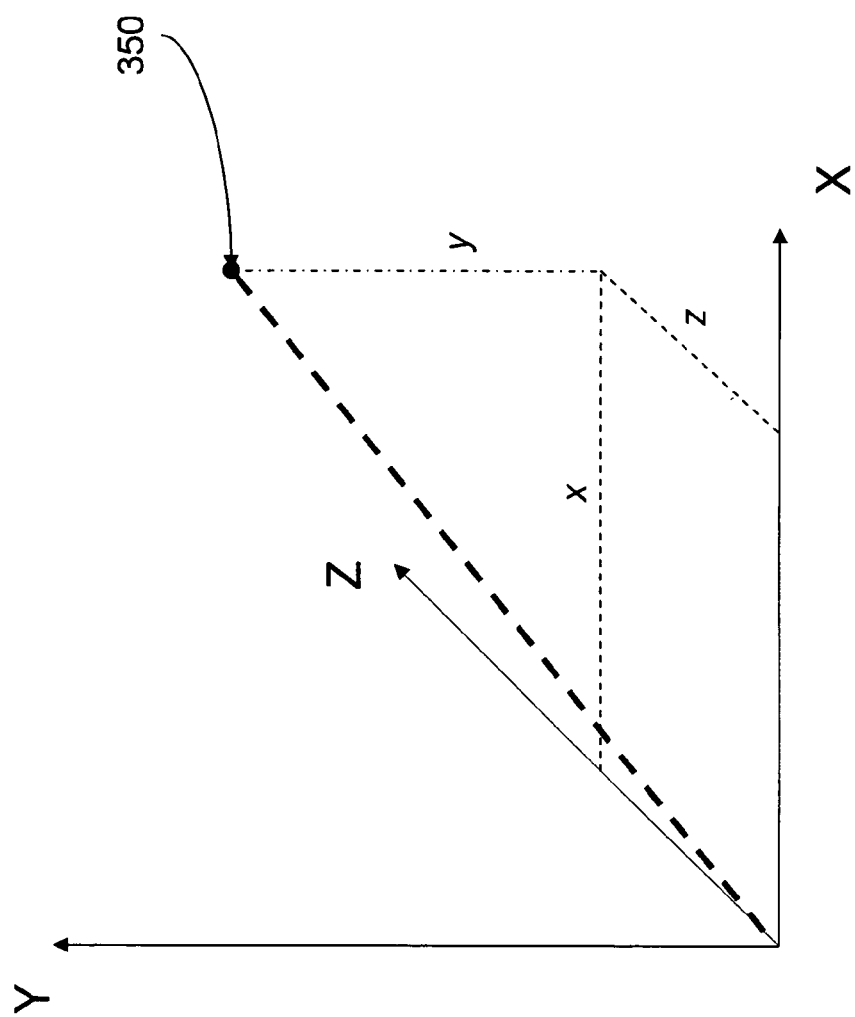
FIG. 13 is a representation of a parameter set as a feature vector in a 3 dimensional feature space.

As noted above, in an embodiment of the present invention a parameter set made up of multiple parameter measurements may be represented or modeled as a vector in an n-dimensional feature space. FIG. 13 shows a feature vector 350, representative of the parameter set of a cell, in a 3 dimensional space. The space has three axes x, y and z and the feature vector 350 has three dimensions x, y, z representative of three parameters, such as those listed above, and in the parameter set are assigned measurement values taken from the image of a cell. These measurement values are translated into the dimensions of the vector.

Each cell identified from image data has identification data and an associated vector representative of the cell's parameter set. A sample of cells analysed according to the method of the present invention would result in a multiplicity of vectors occupying one feature space. If the parameters for which measurements are taken are indicative of the desired cell classification, the vectors will form clusters, indicating that the parameters are reliable classifying markers. The clusters may fill the entire feature space, and the borders between the clusters can be set to form decision boundaries.

For example, in the embodiment of the invention in which the method is applied to analyse the cell cycle phases of a sample of cells, the parameters for which measurements were taken are all related to markers of cell cycle phase change, (e.g. cell-cycle phase specific protein phosphorylation, such as histone H3 phosphorylation). Hence, the vectors that represent each cell would cluster according to the cell cycle phase of the cell from which the parameter set is derived. Consequently, for each different subpopulation identified in a sample (in the present example, 'prophase', 'metaphase', 'anaphase', 'telophase', 'G2', 'S', 'G2'), there would be a distinct cluster of points in the feature space modeled for the sample.

Classification of Further Sets of Cells

Step 8 of FIG. 1 is the classification of a second set of cells based on the classifying data derived from user-led identification of a first set of cells.

As described above, individual cells are identified and the identifying data is then related to parameter sets that are in turn represented as vectors in a feature space. Cells that are identified by the user are considered to be the 'training set', on which a system according to the present invention stores parameter sets in association with the user-entered identifying data, to derive classifying data. Once a suitably large database of classifying data has been built up from user identification of cells, the system may be instructed to perform automated classification. As described with reference to step 8 of FIG. 1, automated classification consists of analysis of a second set of cells, the analysis involving division into object areas, and the taking of measurements in a manner similar to steps 1 and 2. The measurements are then analysed and the second set of cells are divided into subpopulations, on the basis of the measurements taken for cells in the second set of cells, by use of the cell classifying data.

The division into subpopulations may involve simple comparisons of the measurement values for a parameter. For example, if all mitotic cells in the training set had a measured value of a for parameter B, any cells to be classified in the second set that have a sufficiently similar measured value of a for parameter B will also be classed as mitotic. However, the measurements values of cells in the second set will rarely tally exactly with the measurement values in parameter sets from the training set, due to normal biological variation. Therefore, in order to divide the second set into subpopulations, in an embodiment statistical techniques are employed to calculate which subpopulation that each cell in the second set should be classified in.

If each parameter set derived from the training set is represented as a vector in a feature space, as described above, the feature vectors will cluster in the feature space according to the classification of the corresponding cell.

Once trained, when a computer system implementing an embodiment of the invention is instructed to classify a set of cells, each cell is identified, analyzed as described above and a feature vector generated from a parameter set derive from its measurements. The feature vector of the cell is then analysed statistically in comparison with the clusters of feature vectors derived from the training set.

In cases where more than one measurement is taken from the image for more than one parameter, one or more of the measurements may be weighted. By weighting the value of a measurement of a parameter, that measurement has a more significant effect on the outcome of the classification. For example, if the measurements of three parameters a, b and c are taken and a is known to be a more reliable indicator of cell cycle phase, the value of a may be altered to so that a has a proportionately greater effect on the results of an algorithm that uses the parameter set a, b, c to classify cells according to cell cycle phase. Weighting has the further advantage of minimizing classification error that may be caused by variation in the value of unweighted measurements. The weighting may take the form of multiplication of the value of the measurement. The parameter measurements may also be normalized to correct for parameters with dominant values.

Figure 14:
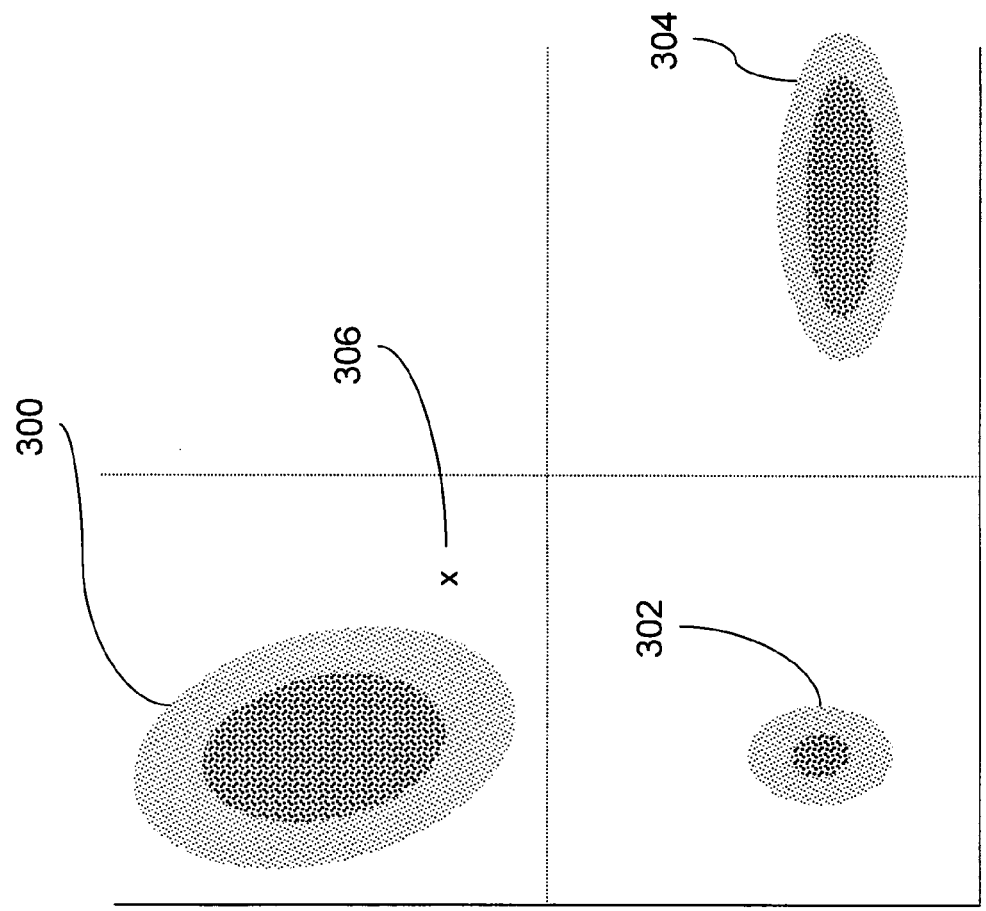
FIG. 14 is a representation of feature vector in a 2 dimensional space, with clusters of pre-classified feature vectors.

One method of statistical analysis is minimum distance classification. In this case, a cell from the second set will be classified into a subpopulation based on the minimum distance between its feature vector and the clusters. The cell to be classified is classified in the same subpopulation as the feature vectors that make up the cluster that is nearest to the feature vector. FIG. 14 illustrates a feature space in which minimum distance classification may be implemented. FIG. 14 illustrates a two dimensional feature space with three clusters 300, 302 and 304 formed from the feature vectors of training sets. Each cluster is representative of a different subpopulation. Vector 306 (shown as a cross marking x and y values) is derived from the parameter set of a cell from a set which is to be classified. Each cluster is modeled according to its centre of mass, represented as the mean feature vector for the cluster. In the case of FIG. 14, representing a two dimensional feature space, the mean feature vector is at the geometrical centre of each cluster. The feature vector is classified according to the mean feature vector nearest to it (the minimum distance). In this case, the mean feature vector of cluster 300 is nearest to feature vector 306 and so the cell which feature vector 306 is representative of would be classified in the same subpopulation as cluster 300.

In the case of a two dimensional feature space (ie. where only two parameters of the cell image data have been measured), calculation of the distance between two points is relatively straightforward. There are a number of techniques to measure the distance between two points in multi-dimensional space. These measures are known as similarity metrics.

The most commonly used similarity metric is the Euclidean distance. If $x_1$ and $x_2$ are two vectors whose similarity is to be checked then the Euclidean distance is defined as:

$$d_e = \sqrt{\sum_{i=1}^{N} (x_1^{(i)} - x_2^{(i)})^2}.$$

The Euclidean distance measure has the property of giving greater emphasis to larger differences on a single parameter. The classification can thus be biased towards a parameter with dominant values. To overcome this problem, parameter measurements can be normalized and/or otherwise weighted using known statistical techniques prior to creating a feature vector.

Alternatively, if speed of processing is a priority, the city block or interpoint distance metric may be implemented. The city block distance is also known as the absolute value distance or 'Manhattan' distance. The city block distance is computationally cheaper to calculate than the Euclidean distance. The city block distance is defined as:

$$d_i = \sum_{i=1}^{N} |x_1^{(i)} - x_2^{(i)}|.$$

The Chebyshev distance metric is also computationally cheaper than the Euclidean distance. It is defined as:

$$d_{ch} = \max_i |x_1^{(i)} - x_2^{(i)}|.$$

A variant using the Mahalanobis distance may also be implemented. The Mahalanobis distance can be defined as:

$$d_m = \sqrt{\ln|\Sigma_i| + (x_i - m_i)^t \Sigma_i^{-1}(x_i - m_i)}.$$

The Mahalanobis distance metric has some useful properties. It automatically accounts for the scaling of the axes of the feature space, and corrects for correlation between related parameters (parameters whose measurement values are to a degree interdependent e.g. the concentration of products of genes which are co-regulated.) The Mahalanobis distance metric can also accommodate curved decision boundaries (borders between clusters). However, computational requirements for the Mahalanobis distance metric grow quadratically with the number of parameters.

In the case of a highly complex feature space, a minimum distance similarity metric such as those described above may not be able to adequately classify feature vectors into clusters. Parameter choice will affect the complexity of the feature space.

As an alternative to minimum distance calculation in any form, a feature vector may be classified using the Bayesian maximum likelihood algorithm. This algorithm is a special case of the general Bayes' classification, based on Bayes' theorem. The subpopulations into which cells are classified are denoted $\overline{\omega}_i$, i=1, 2, . . . , m where m is the total number of classes. When trying to determine which subpopulation a cell represented by a feature vector at position x in feature space belongs to one can define a conditional probability for each potential class:

$p(\overline{\omega}_i|x)$ i=1, 2, . . . , m.

The feature vector x may be shown as a column vector of parameter measurements (feature 1, feature 2, up to feature n) that locates x in a multidimensional feature space, for example:

$$x = \begin{bmatrix} \text{feature 1} \\ \text{feature 2} \\ \vdots \\ \text{feature n} \end{bmatrix}.$$

The conditional probability $p(\overline{\omega}_i|x)$ gives the likelihood that the sample at position x belongs to class $\overline{\omega}_i$. Classification can then be performed according to:

$x \in \overline{\omega}_i$ if $p(\overline{\omega}_i|x) > p(\overline{\omega}_j|x)$ for all $j \neq i$ i.e. the sample belongs to class $\overline{\omega}_i$ if $p(\overline{\omega}_i|x)$ is the greatest.

The conditional probabilities in the above equation are initially unknown. However, if the training data set is available, a probability distribution function (PDF) for each type can be estimated. This PDF describes the chance of finding a feature vector from class $\overline{\omega}_i$ at position x. In general terms this further probability can be represented by $p(x|\overline{\omega}_i)$. Therefore, for a feature vector at position x in multidimensional space, a set of probabilities can be computed that gives the relative likelihood that that feature vector belongs to a class $\overline{\omega}_i$.

The desired $p(\overline{\omega}_i|x)$ and the available $p(x|\overline{\omega}_i)$ are related by Bayes' theorem:

$$p(\varpi_i | x) = \frac{p(x | \varpi_i) p(\varpi_i)}{p(x)},$$

where $p(\overline{\omega}_i)$ is the a-priori probability that class $\overline{\omega}_i$ occurs in the image and $p(x)$ is the probability of finding a sample of any class at location x. Substituting the above equations gives the classification rule:

$x \in \overline{\omega}_i$ if $p(x|\overline{\omega}_i)p(\overline{\omega}_i) > p(x|\overline{\omega}_j)p(\overline{\omega}_j)$ for all $j \neq i$.

With one modification for mathematical convenience, we can define the discriminant function $g_i(x)$:

$$g_i(x) = \ln\{p(x|\varpi_i)p(\varpi_i)\}$$
$$= \ln p(x|\varpi_i) + \ln p(\varpi_i)$$

The classification rule can thus be restated as:

$x \in \overline{\omega}_i$ if $g_i(x) > g_j(x)$ for all $j \neq i$.

The implementation of a Bayesian method for determining the classification of a feature vector has the advantage that multiple parameters may be used, increasing the granularity of classification by allowing division of cells into a greater amount of subpopulations.

A quadratic or non-linear discriminant (QD) classifier may be used to classify cells into subpopulations. A QD classifier is described in Thomaz, C., Gillies, D. F., and Feitosa, R. Q., Proc. Post-ECCV Workshop on Biometric Authentication (2002.) The QD classifier stipulates that an unknown feature vector x is assigned to the class or group I that minimizes a function $d_i(x)$ dependent upon the true mean vector and the covariance matrix. This method of classification performs comparatively well with a limited amount of training data, and can also readily be used where measurements have been taken for a multiplicity of parameters.

Further techniques classification that maybe employed either alone or in combination with the above techniques include multivariate Gaussian class models (for the evaluation of results from Bayesian classification), density estimation, and K-nearest neighbour classification (Therrien, C. W., *Decision, estimation and classification*, John Wiley & Sons, 1989).

Neural networks may also be implemented in order to classify within complex feature spaces. A neural network is a mathematical model for information processing based on the bioelectrical networks in the brain, which are formed by neurones and their synapses. In a neural network model, simple nodes (or "neurons", or "units") are connected together to form a network of nodes—hence the term "neural network".

The most common learning technique employed with neural networks is backpropagation. The output values are compared with the correct answer to compute the value of a predefined error-function. By various techniques the error is then fed back through the network. Using this information, an algorithm including the network adjusts the weights of each connection between nodes in order to reduce the value of the error-function by a small amount. After repeating this process for a sufficiently large number of training cycles the network will usually converge to some state where the error of the calculations is small. In this case one says that the network has learned a certain target function. To adjust weights properly a general method for nonlinear task optimization known as gradient descent may be applied. In this method, the derivation of the error-function with respect to the network connection weights is calculated and the weights are then changed such that the error decreases (thus going downhill on the surface of the error function).

Creating a neural network that performs well, particularly in classifying examples that differ significantly from the training examples, often requires additional techniques. This is especially important for cases where only very limited numbers of training examples are available. The network may 'overfit' the training data by creating a statistical model of the data that has too many parameters, and thereby fail to capture the true statistical process generating the data. To counteract overfitting an 'early stopping heuristic' can ensure that the network will generalize well to examples not in the training set. It should also be noted that neural networks generally require a greater amount of training data than minimum distance metric classification methods.

Statistical techniques such as canonical variate analysis may be used to reduce the dimensionality of the feature space during processing. A reduced number of dimensions will result in faster processing, and may also facilitate more accurate classification.

It should be understood that any of the above classification methods may be used individually or in combination with each other.

The above embodiments are to be understood as illustrative examples of the invention. Further embodiments of the invention are envisaged.

Note that the term "luminescence" as used herein is intended to include the phenomena of fluorescence and other types of luminescence such as chemiluminescence and phosphorescence.

Multiple images of a cell population may be taken and combined. For example, if a cell population is expressing two fluorophores which fluoresce at differing wavelengths (e.g. DRAQ5 and GFP), two separate images may be taken via two different filters. Parameter measurements may be taken from one or both of the images.

The cell cycle position of the cells may be determined in various alternative embodiments of the invention by monitoring the expression of the reporter molecule and detecting luminescence signals emitted by the reporter using an appropriate detection device. If the reporter molecule produces a fluorescent signal, then, either a conventional fluorescence microscope, or a confocal based fluorescence microscope may be used. If the reporter molecule produces luminous light, then a suitable device such as a luminometer may be used. Using these techniques, the proportion of cells expressing the reporter molecule may be determined.

If the DNA construct contains translocation control elements and the cells are examined using a microscope, the location of the reporter may also be determined.

In methods according to the present invention, the fluorescence of cells transformed or transfected with the DNA construct may suitably be measured by optical means in for example; a spectrophotometer, a fluorimeter, a fluorescence microscope, a cooled charge-coupled device (CCD) imager (such as a scanning imager or an area imager), a fluorescence activated cell sorter, a confocal microscope or a scanning confocal device, where the spectral properties of the cells in culture may be determined as scans of light excitation and emission.

The present invention is not limited to cell cycle analysis using fluorescence imaging. Alternatively, the invention may be employed using brightfield imaging, DIC imaging, phase contrast imaging, etc for the classification of cells, including cell cycle analysis.

The present invention could not only be applied as described above, but could also be applied at the cellular and subcellular level within living or chemically fixed organisms (e.g. zebrafish) which are amenable to imaging within multiwell plates. The techniques of the present invention could also be applied at the cellular level for classifications of microbes, including bacteria and eukaryotic protozoa, growing freely or within eukaryotic cells.

In addition to the above, the techniques of the present invention are also useful for genetic screens in order to identify cells or cell mutants where expression of a particular GFP fusion protein (or proteins using other reporters) is altered in amount (intensity) or location within a cell.

The invention may also be applied by the use of cytoskeleton reporters such as GFP-tubulin, GFP-actin and GFP fused to various intermediate filament proteins. The cytoskeleton varies dramatically according to the cell cycle (e.g. microtubules change from a radial array into a mitotic spindle) and the intensity and spatial characteristics of these arrays can be used in combination, or separately, from the cell cycle markers described herein.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method of classifying cells into subpopulations using cell classifying data, the method comprising:
receiving image data;
analyzing said image data to identify object areas in the image data;
analyzing said image data, on the basis of said identified object areas, to determine, for at least one selected first cell, one or more measurements;
deriving a plurality of parameter sets for said at least one selected first cell, wherein the plurality of parameter sets includes at least one of said one or more measurements;
classifying a first set of cells by a user selected classification method, the process of classifying the first set of cells including classifying said at least one selected first cell into a subpopulation by optimizing dimensionality of feature space and storing first identifying data indicating the subpopulation into which said at least one selected first cell has been classified;
deriving cell classifying data for use in classifying a second set of cells into subpopulations from a first parameter set and a first identifying data, and
classifying a second set of cells into subpopulations on the basis of one or more measurements based on at least one of the plurality of parameters sets weighted in relation to the plurality of parameter sets.

2. The method of claim 1, wherein said first identifying data is cell cycle phase classifying data.

3. The method of claim 1, wherein classifying said second set of cells includes comparing the measurements for cells in the second set with the cell cycle phase classifying data derived from classification of the first set of cells.

4. The method of claim 1, wherein classifying said second set of cells comprises calculating a statistical likelihood of each cell in the second set being a member of a subpopulation.

5. The method of claim 1, wherein applying said cell classifying data to a second set of cells further comprises generating cell cycle phase population data indicative of the relative sizes of said plurality of sub-populations in the selected cells.

6. The method of claim 1, further comprising performing the method with image data from a plurality of wells containing cells, the plurality of wells containing different test compounds.

7. The method of claim 1, wherein said object areas are identified using a process arranged to select both nuclear and cytoplasmic areas of a cell.

8. The method of claim 1, wherein said object areas include, for a selected cell, a first type of object area and a second type of object area, and wherein said one or more measurements include a first measurement determined using said first type of object area and a second measurement determined using said second type of object area.

9. The method of claim 8, wherein said first type of object area is identified using a process arranged to select a nuclear area of a cell.

10. The method of claim 8, wherein said second type of object area is identified using a process arranged to select a cytoplasmic area of a cell.

11. The method of claim 1, wherein said one or more measurements include, for a selected cell, a first measurement determined using an identified object area and a second measurement determined using an identified object area.

12. The method of claim 11, wherein said first and second measurements are determined using the same identified object area.

13. The method of claim 1, wherein cells of said first and second sets of cells comprise at least a first luminescent reporter, wherein receiving image data comprises receiving first image data created by detecting radiation emitted by said first luminescent reporter, and wherein analyzing said image data to determine one or more measurements includes analyzing said first image data.

14. The method of claim 13, wherein analyzing said image data to identify object areas comprises analyzing said first image data.

15. The method of claim 13, wherein at least one cell in said first and second sets of cells further comprises a second luminescent reporter indicative of the location of a subcellular component in a cell.

16. The method of claim 13, wherein said one or more measurements include a measurement of a cytoplasmic luminescence signal intensity, taken in an area adjacent to a cytoplasmic component of a selected cell.

17. The method of claim 13, wherein said one or more measurements include a measurement of a nuclear luminescence signal intensity, taken in an area adjacent to a nuclear component of a selected cell.

18. The method of claim 13, wherein analyzing said image data to identify object areas comprises analyzing said first image data.

19. The method of claim 1, wherein receiving image data comprises:
   a) receiving first image data created by detecting radiation emitted by said first luminescent reporter; and
   b) receiving second image data created by detecting radiation emitted by said second luminescent reporter,
      wherein said step of analyzing said image data to identify object areas comprises analyzing said second image data, and
      wherein said step of analyzing said image data to determine one or more measurements comprises analyzing said first image data.

20. The method of claim 1, wherein said cell classifying data is used in conjunction with an algorithm to classify a selected cell into a selected first one of a plurality of sub-populations of cells.

21. The method of claim 20, wherein the algorithm takes into account a plurality of measurements in a parameter set.

22. The method of claim 1, wherein said one or more measurements include one or more measurements of the plurality of parameters selected from the group consisting of:
   I, a parameter relating to an average signal intensity within an identified object area;
   F, a parameter relating to a fraction of pixels that deviate more than a given amount from an average signal intensity within an identified object area;
   H, a parameter relating to the number of pixels with a signal intensity below a given threshold within an identified object area;
   A, a parameter relating to a ratio between major and minor axes of an elliptical outline corresponding to an identified object area;
   R, a parameter relating to a maximum width of an identified object area;
   L, a parameter relating to an average width of an identified object area;
   C, a parameter relating to signal texture within an identified object area;
   M, a parameter relating to margination in an identified object area.

23. The method of claim 1, wherein a second parameter set is derived from said one or more measurements taken for the second set of cells.

24. The method of claim 23, further comprising the modeling of a parameter set as a feature vector in an n-dimensional feature space, where n is equal to the number of parameters.

25. The method of claim 24, wherein a feature vector representing said second parameter set and a feature vector representing said first parameter set occupy the same feature space.

26. The method of claim 25, wherein a distance is calculated between the feature vectors.

27. The method of claim 26, wherein the distance between the feature vectors is indicative of the classification of the feature vector representing the second parameter set.

28. The method of claim 25, wherein a neural network is applied to classify the cell represented by a feature vector representing the second parameter set with respect to the feature vector representing the first parameter set.

29. The method of claim 24, wherein a cell represented by a feature vector representing the second parameter set is classified according to a calculation of probability.

30. The method of claim 29, wherein the calculation of probability comprises calculating the likelihood that the cell represented by said feature vector representing the second parameter set is in the same subpopulation as a cell represented by a feature vector representing the first parameter set, the calculation being based on the dimensions of the feature vectors.

31. The method of claim 1, wherein said cells comprise a nucleic acid reporter construct, preferably a DNA construct, comprising a nucleic acid sequence encoding a detectable live-cell reporter molecule operably linked to and under the control of:
   i) at least one cell cycle phase-specific expression control element, and
   ii) a destruction control element.

* * * * *